United States Patent
Sohn et al.

(10) Patent No.: US 10,327,886 B2
(45) Date of Patent: Jun. 25, 2019

(54) ACCOMODATIVE INTRAOCULAR LENS

(71) Applicant: RAINBOW MEDICAL LTD., Herzliya (IL)

(72) Inventors: Zev Sohn, Ginot Shomron (IL); Yossi Gross, Moshav Mazor (IL)

(73) Assignee: RAINBOW MEDICAL LTD., Herzliya (IL)

(*) Notice: Subject to any disclaimer, the term of this patent is extended or adjusted under 35 U.S.C. 154(b) by 0 days.

(21) Appl. No.: 15/170,417

(22) Filed: Jun. 1, 2016

(65) Prior Publication Data
US 2017/0348094 A1  Dec. 7, 2017

(51) Int. Cl.
*A61F 2/16* (2006.01)

(52) U.S. Cl.
CPC .......... *A61F 2/1629* (2013.01); *A61F 2/1624* (2013.01); *A61F 2/1648* (2013.01); *A61F 2230/0006* (2013.01)

(58) Field of Classification Search
CPC ..... A61F 2/1629; A61F 2/1624; A61F 2/1648
See application file for complete search history.

(56) References Cited

U.S. PATENT DOCUMENTS

| | | | |
|---|---|---|---|
| 4,704,125 A | 11/1987 | Ruminson | |
| 4,711,638 A | 12/1987 | Lindstrom | |
| 4,778,463 A | 10/1988 | Hetland | |
| 4,863,465 A | 9/1989 | Kelman | |
| 4,950,289 A | 8/1990 | Krasner | |
| 5,275,623 A | 1/1994 | Sarfarazi | |
| 5,824,074 A | 10/1998 | Koch | |
| 5,968,094 A | 10/1999 | Werblin et al. | |
| 6,013,101 A | 1/2000 | Israel | |
| 6,117,171 A | 9/2000 | Skottun | |

(Continued)

FOREIGN PATENT DOCUMENTS

| CN | 201015617 Y | 2/2008 |
|---|---|---|
| WO | 2009/021326 A1 | 2/2009 |

(Continued)

OTHER PUBLICATIONS

International Search Report and Written Opinion issued in PCT/IL2017/050594, dated Aug. 30, 2017.

(Continued)

*Primary Examiner* — Leslie Lopez
(74) *Attorney, Agent, or Firm* — Sughrue Mion, PLLC

(57) ABSTRACT

An accommodating intraocular lens implant includes (a) a posterior lens unit and (b) an anterior assembly, which includes first and second anterior components, each of which comprises exactly one polymeric piece. The first anterior component is shaped so as to define an anterior floating lens unit and levers. The second anterior component (a) is assembled with the first anterior component such that the first and the second anterior components are separable from each other without tearing the anterior components, and (b) is shaped so as to define (i) an anterior rim complex, and (ii) anterior rim links, which are connected to the anterior rim complex. The levers are in jointed connection with the anterior floating lens unit, the anterior rim links, and the posterior lens unit. The levers are arranged to move the anterior floating lens unit toward and away from the anterior rim complex.

7 Claims, 17 Drawing Sheets

(56) References Cited

U.S. PATENT DOCUMENTS

| | | | |
|---|---|---|---|
| 6,231,603 | B1 | 5/2001 | Lang et al. |
| 6,423,094 | B1 | 7/2002 | Sarfarazi |
| 6,464,725 | B2 | 10/2002 | Skottun |
| 6,488,708 | B2 | 12/2002 | Sarfarazi |
| 6,524,340 | B2 | 2/2003 | Israel |
| 6,660,035 | B1 | 12/2003 | Lang et al. |
| 6,767,363 | B1 | 7/2004 | Bandhauer et al. |
| 6,884,263 | B2 | 4/2005 | Valyunin et al. |
| 7,223,288 | B2 | 5/2007 | Zhang et al. |
| 7,238,201 | B2 | 7/2007 | Portney et al. |
| 7,416,562 | B2 | 8/2008 | Gross |
| 7,871,437 | B2 | 1/2011 | Hermans et al. |
| 2002/0107568 | A1 | 8/2002 | Zadno-Azizi et al. |
| 2002/0111678 | A1 | 8/2002 | Zadno-Azizi et al. |
| 2003/0109925 | A1 | 6/2003 | Ghazizadeh et al. |
| 2003/0204255 | A1* | 10/2003 | Peng .................... A61F 2/1613 623/6.34 |
| 2004/0082993 | A1 | 4/2004 | Woods |
| 2004/0148023 | A1 | 7/2004 | Shu |
| 2006/0001186 | A1 | 1/2006 | Richardson et al. |
| 2007/0156236 | A1 | 7/2007 | Stenger |
| 2008/0051886 | A1 | 2/2008 | Lin |
| 2008/0097461 | A1 | 4/2008 | Boukhny et al. |
| 2009/0228101 | A1 | 9/2009 | Zadno-Azizi |
| 2011/0071628 | A1 | 3/2011 | Gross et al. |
| 2011/0295368 | A1 | 12/2011 | Betser |
| 2013/0184816 | A1 | 7/2013 | Hayes |
| 2013/0197636 | A1 | 8/2013 | Haefliger |
| 2014/0052246 | A1 | 2/2014 | Kahook et al. |
| 2014/0180407 | A1 | 6/2014 | Sohn et al. |
| 2014/0309734 | A1* | 10/2014 | Sohn .................... A61F 2/1648 623/6.34 |
| 2014/0309735 | A1 | 10/2014 | Sohn et al. |
| 2016/0015648 | A1 | 1/2016 | Gross et al. |

FOREIGN PATENT DOCUMENTS

| | | | |
|---|---|---|---|
| WO | 2009/021327 | A1 | 2/2009 |
| WO | 2010/089689 | | 8/2010 |
| WO | 2013/016804 | A1 | 2/2013 |
| WO | 2013/126986 | A1 | 9/2013 |
| WO | 2015/198236 | | 12/2015 |
| WO | 2016/161519 | A1 | 10/2016 |
| WO | 2017/181295 | A1 | 10/2017 |
| WO | 2017/208230 | A1 | 12/2017 |

OTHER PUBLICATIONS

Invitation to Pay Additional Fees dated Oct. 9, 2015, which issued during the prosecution of Applicant's PCT/IB2015/054730.

International Search Report and Written Opinion in PCT/IB2015/054730, dated Dec. 28, 2015.

An Office Action dated Feb. 2, 2015, which issued during the prosecution of U.S. Appl. No. 14/139,579.

McLeod SD et al., "Synchrony dual-optic accommodating intraocular lens Part 1: Optical and biomechanical principles and design considerations," J Cataract Refract Surg. 2007; 33:37-46.

Ossma IL et al., "Synchrony Dual-Optic Accommodating Intraocular Lens Part 2: Pilot Clinical Evaluation," J Cataract Refract Surg. 2007; 33:47-52.

Crystalens 5.0 (Model AT-50SE), Mar. 2007.

Crystalens, Don't just see. See better, pp. 1-3, Sep. 2009.

U.S. Appl. No. 61/150,762, filed Feb. 8, 2009.

An International Search Report dated Jun. 18, 2010, which issued during the prosecution of Applicant's PCT/IB2010/050421.

StabilEyes® Capsular Tension Ring, Abbott Medical Optics, http://www.amo-inc.com/products/cataract/supportsystems/stabileyes-capsular-tension-ring, downloaded Mar. 9, 2014.

An Office Action dated Aug. 2, 2011, which issued during the prosecution of U.S. Appl. No. 12/566,029.

An Office Action dated May 5, 2011, which issued during the prosecution of U.S. Appl. No. 12/566,029.

An Office Action dated Jan. 27, 2012, which issued during the prosecution of U.S. Appl. No. 12/566,029.

An Office Action dated Jul. 15, 2015, which issued during the prosecution of U.S. Appl. No. 14/315,301.

An Office Action dated May 26, 2016, which issued during the prosecution of U.S. Appl. No. 14/315,301.

An Office Action dated Oct. 30, 2015, which issued during the prosecution of U.S. Appl. No. 14/315,301.

An Office Action dated Nov. 5, 2014, which issued during the prosecution of U.S. Appl. No. 14/139,579.

Still image excerpts from Modular IOL Video, ClarVista Medical, posted to YouTube.com on Dec. 5, 2013 (https://www.youtube.com/watch?v=-dAAPFHOqRQ).

TECNIS® 3-Piece IOL, Abbott Medical Optics, http://www.amo-inc.com/products/cataract/monofocal-iols/tecnisaspheric-iol, downloaded Mar. 9, 2014.

Krader CG, "Modular IOL system begins clinical evaluation," Ophthalmology Times, Jan. 2014.

Interview Summary Report dated Feb. 18, 2016, which issued during the prosecution of U.S. Appl. No. 14/315,301.

Interview Summary Report dated Jun. 14, 2016, which issued during the prosecution of U.S. Appl. No. 14/315,301.

An Interview Summary dated Jul. 6, 2017, which issued during the prosecution of U.S. Appl. No. 14/315,301.

An Interview Summary dated Jan. 10, 2017, which issued during the prosecution of U.S. Appl. No. 14/315,301.

An Office Action dated May 5, 2017, which issued during the prosecution of U.S. Appl. No. 14/315,301.

An Advisory Action dated Oct. 27, 2016, which issued during the prosecution of U.S. Appl. No. 14/315,301.

A non-final office action issued in U.S. Appl. No. 15/125,916, dated Jun. 28, 2018.

An Extended European search report issued in European Appl. 15811584.0, dated Jan. 4, 2018.

Non-Final Office Action issued in U.S. Appl. No. 15/125,916, dated Jan. 29, 2018.

ISR and Written Opinion issued in International Appl. PCT/IL2017/051317, dated Feb. 26, 2018.

An Office Action dated Aug. 27, 2018, which issued during prosecution of U.S. Appl. No. 15/393,947.

An Office Action dated Nov. 16, 2018, which issued during prosecution of U.S. Appl. No. 15/125,916.

* cited by examiner

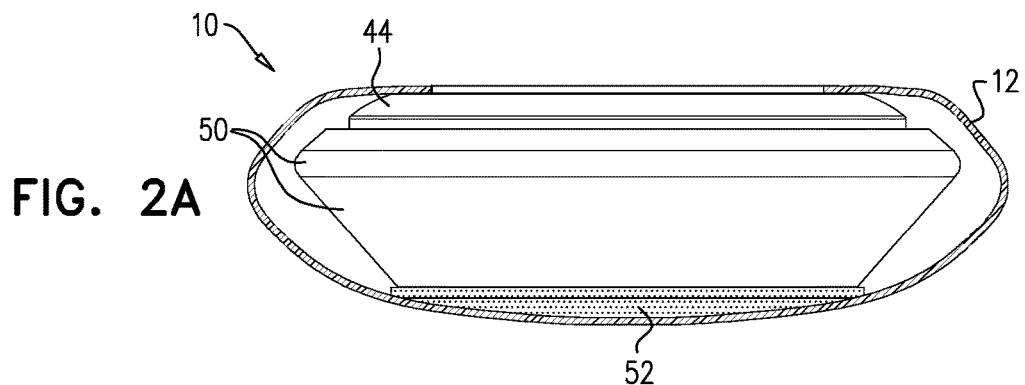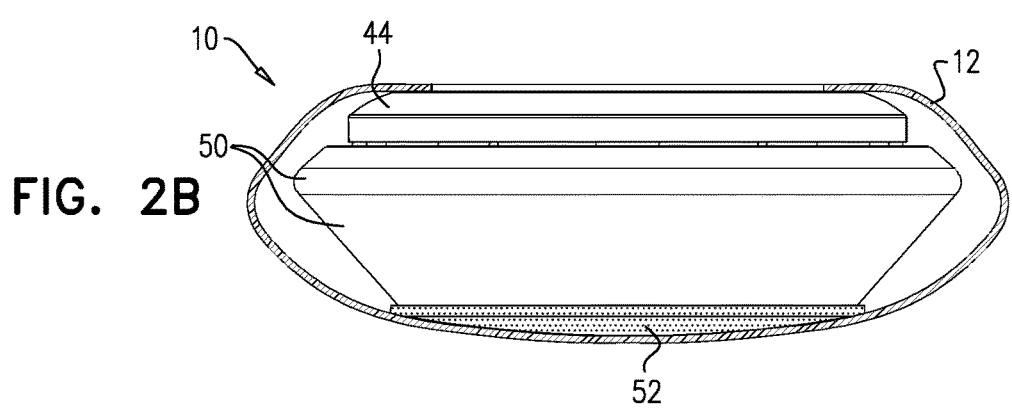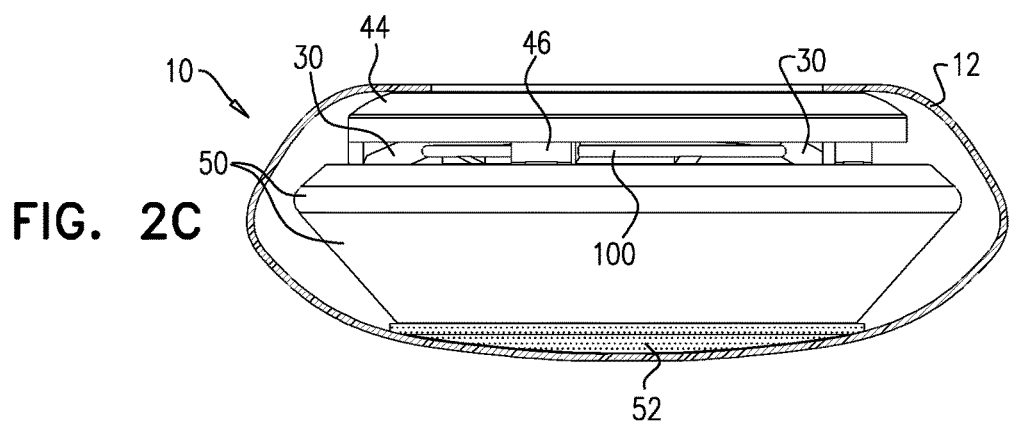

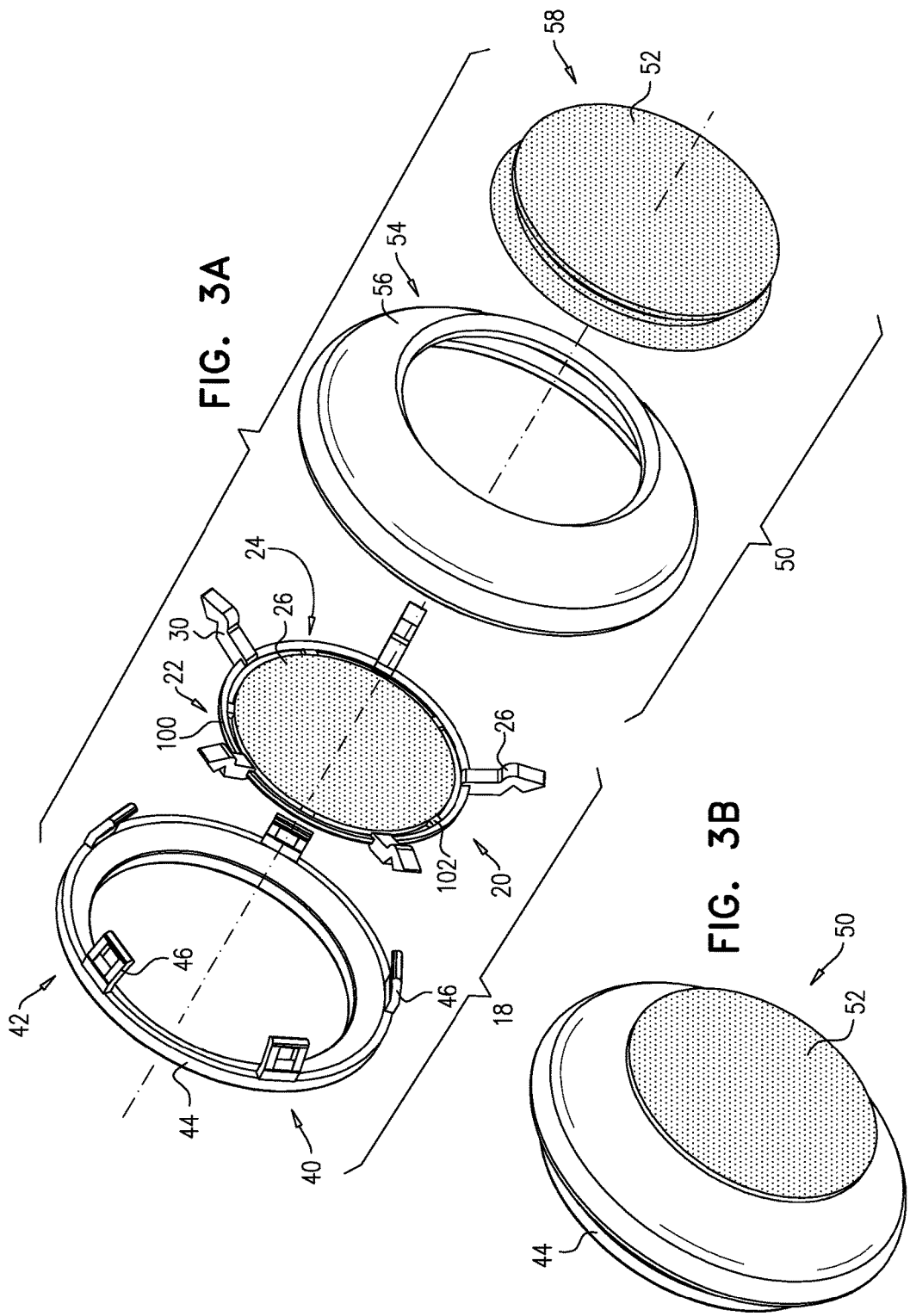

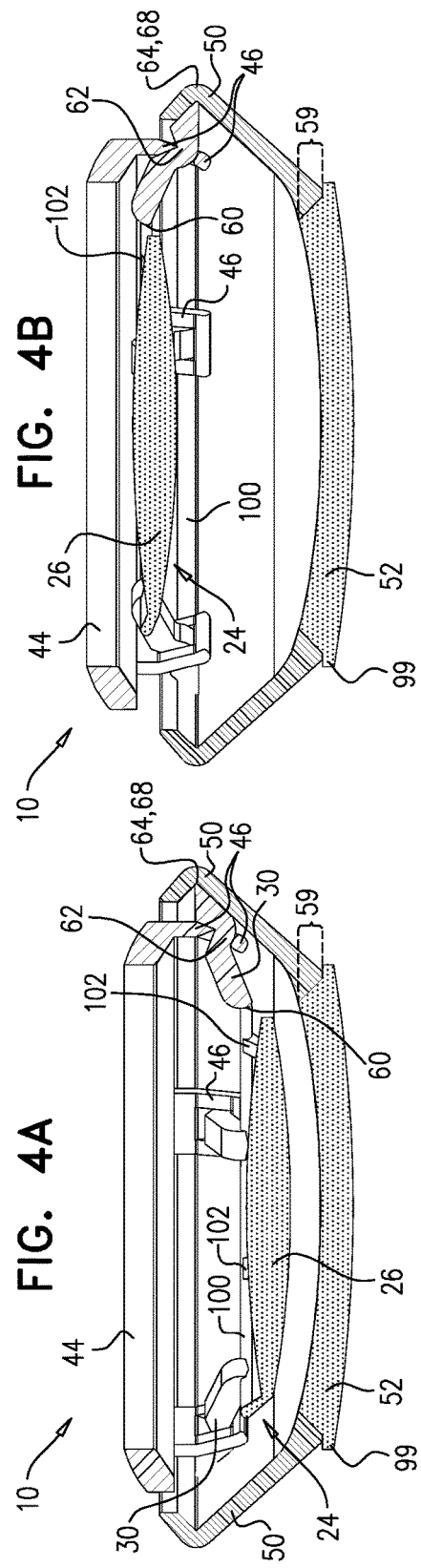

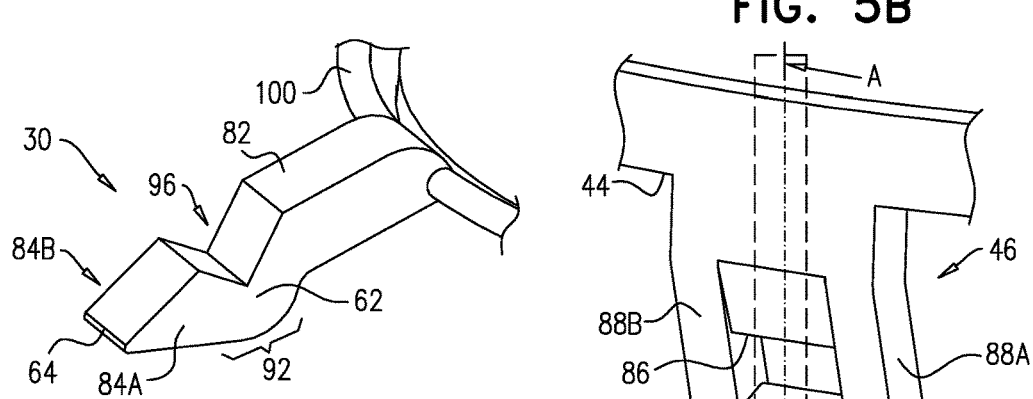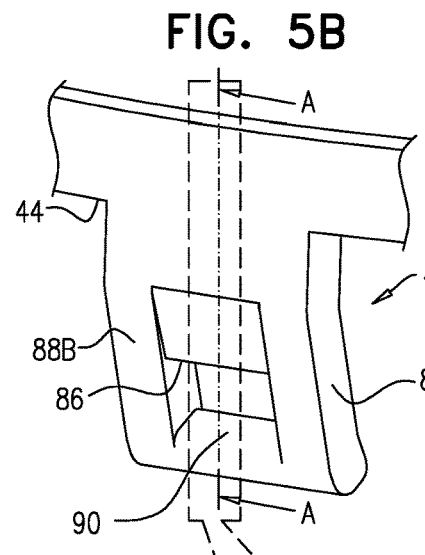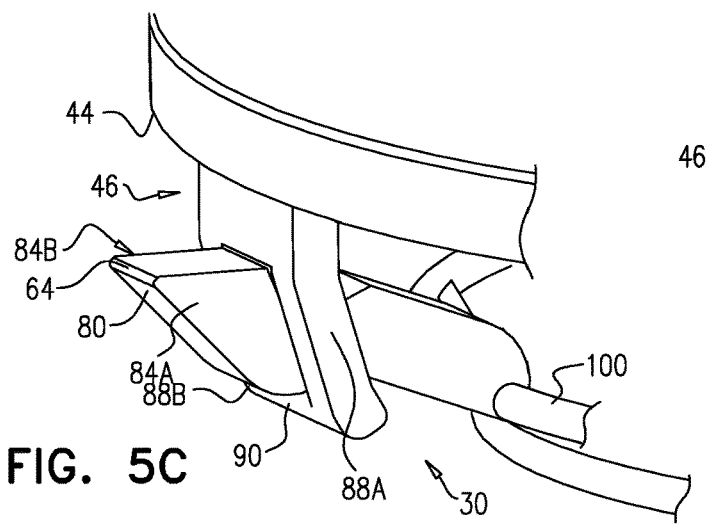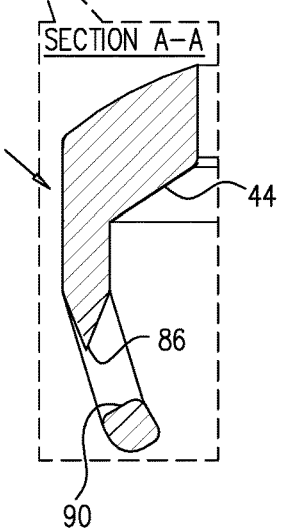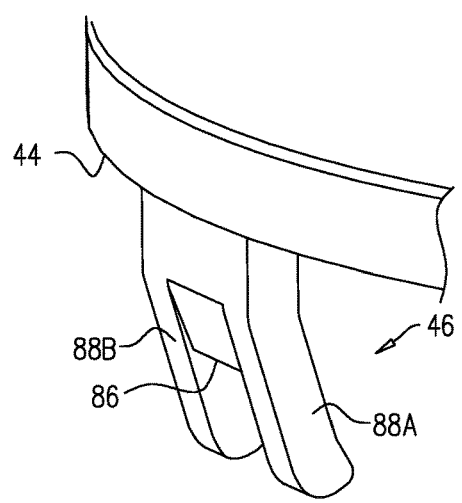

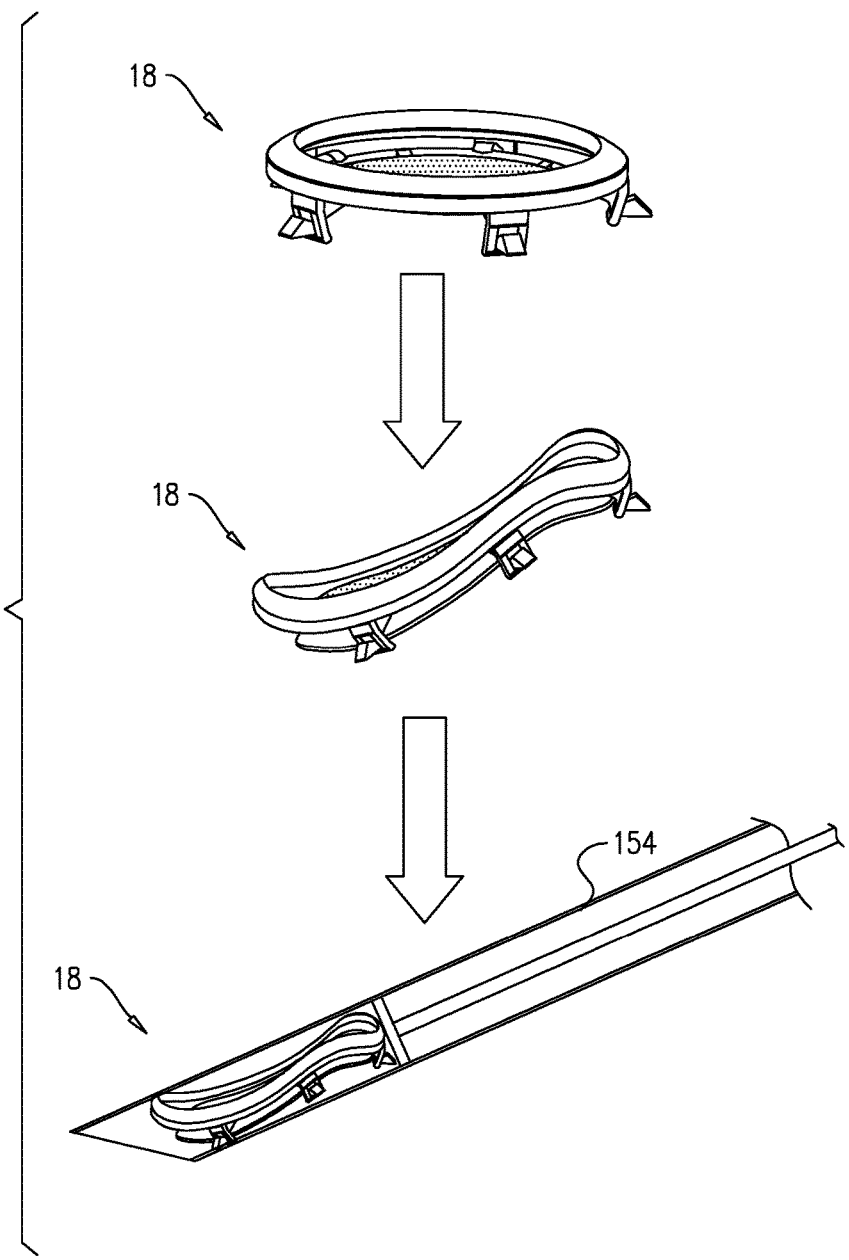

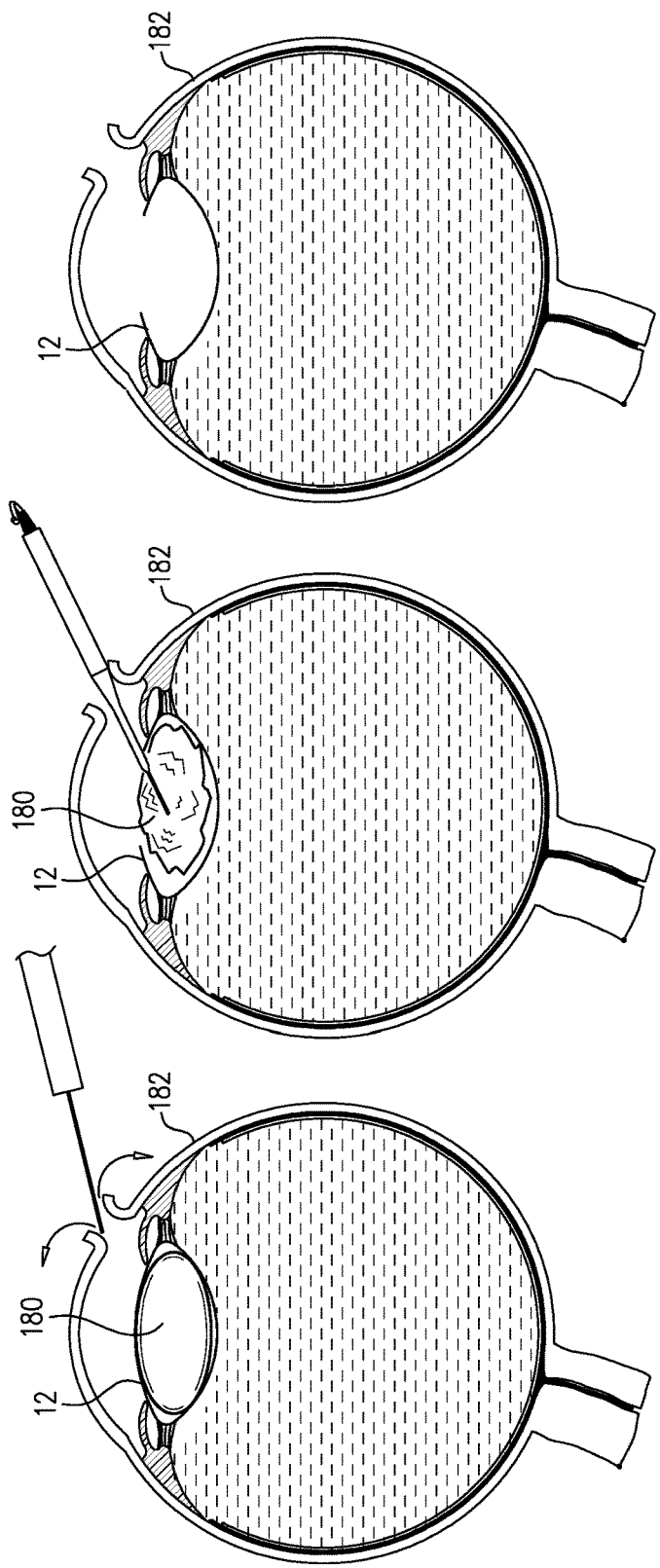

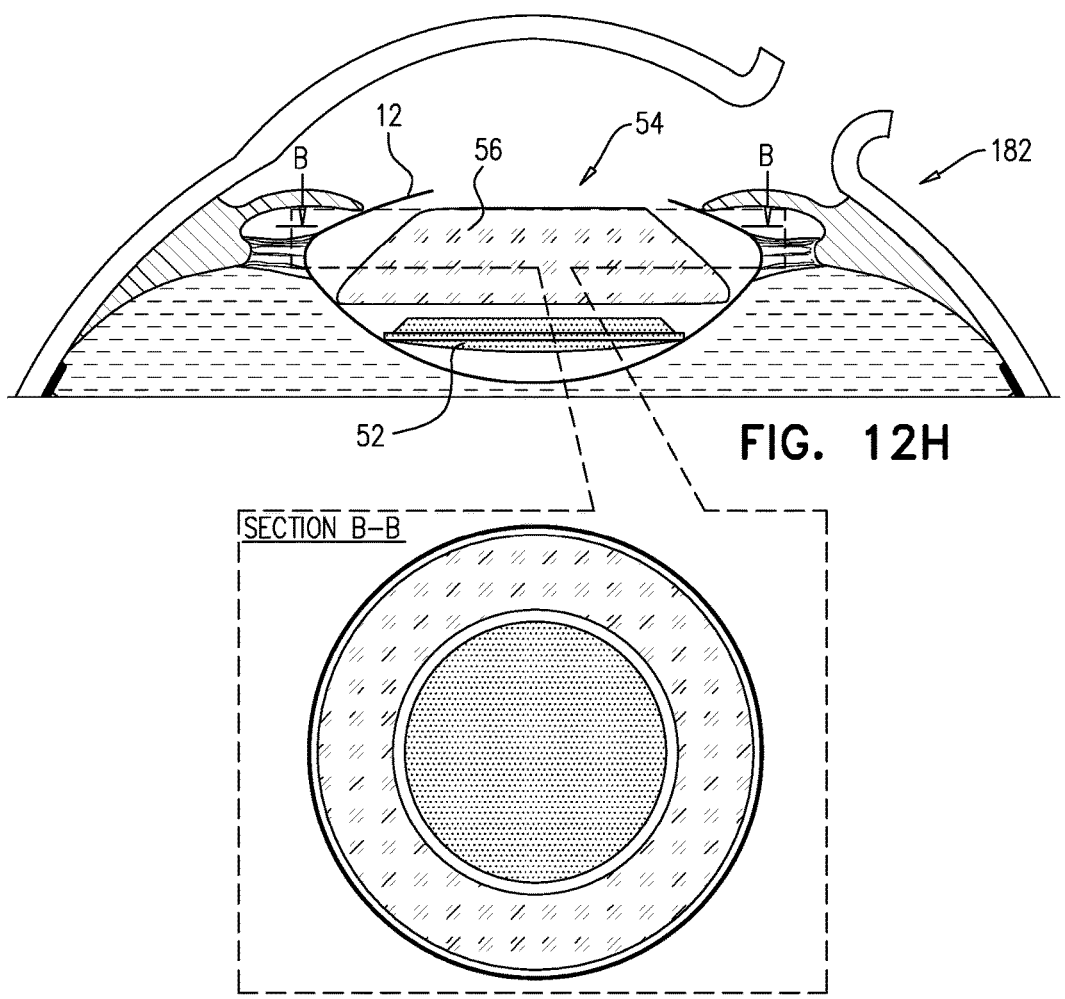

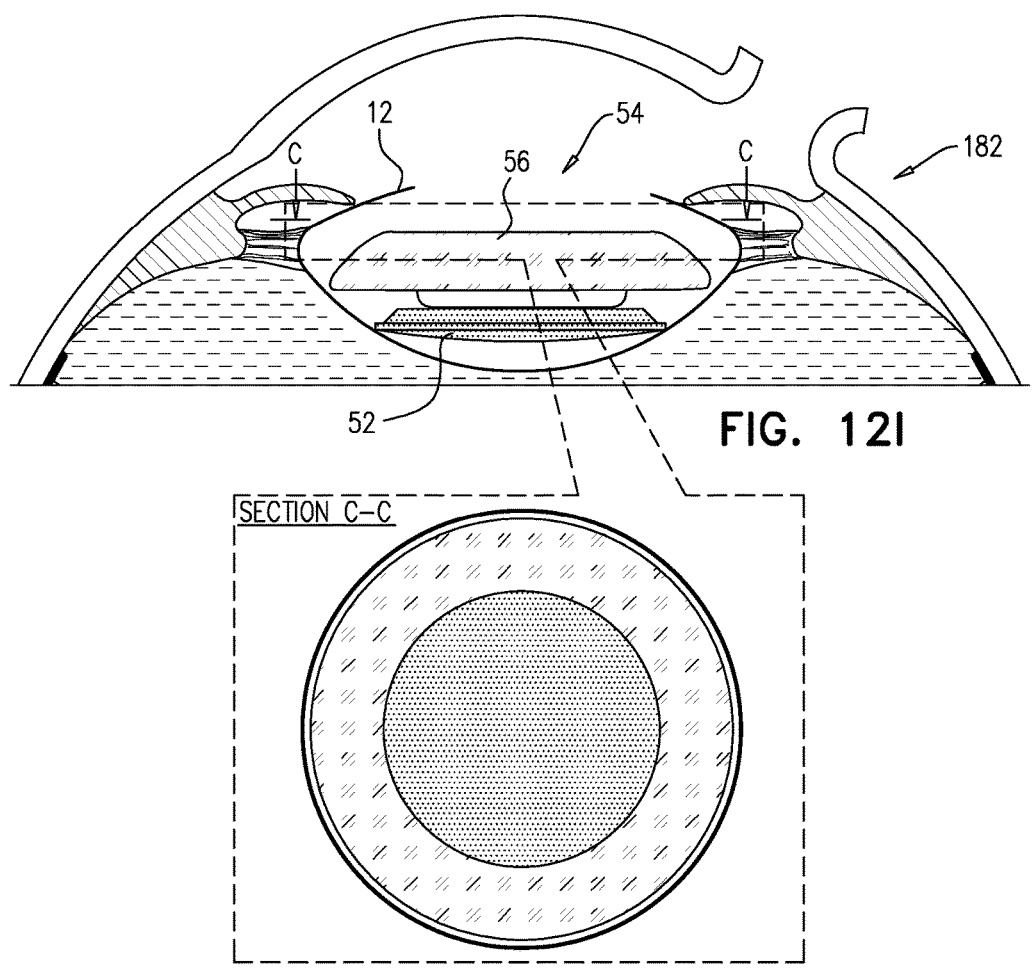

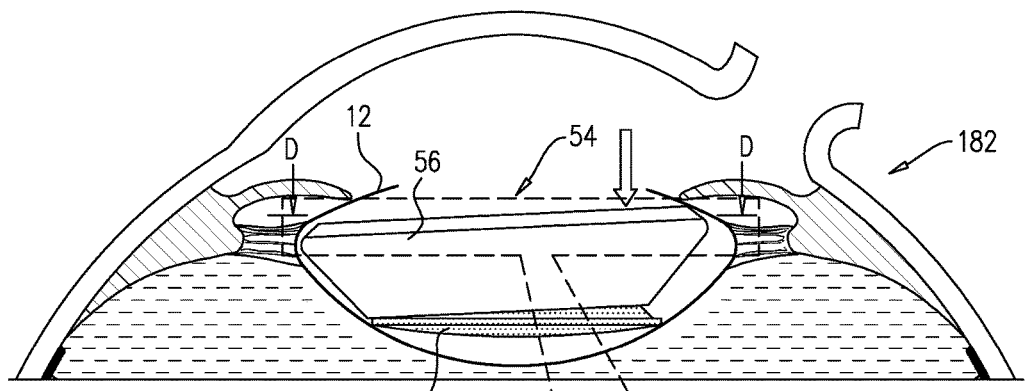
FIG. 12J
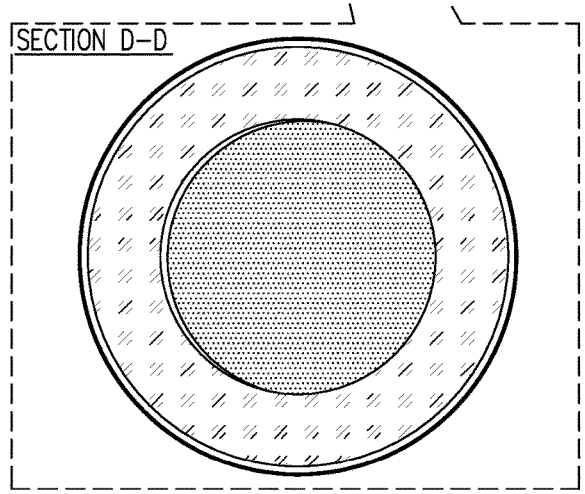
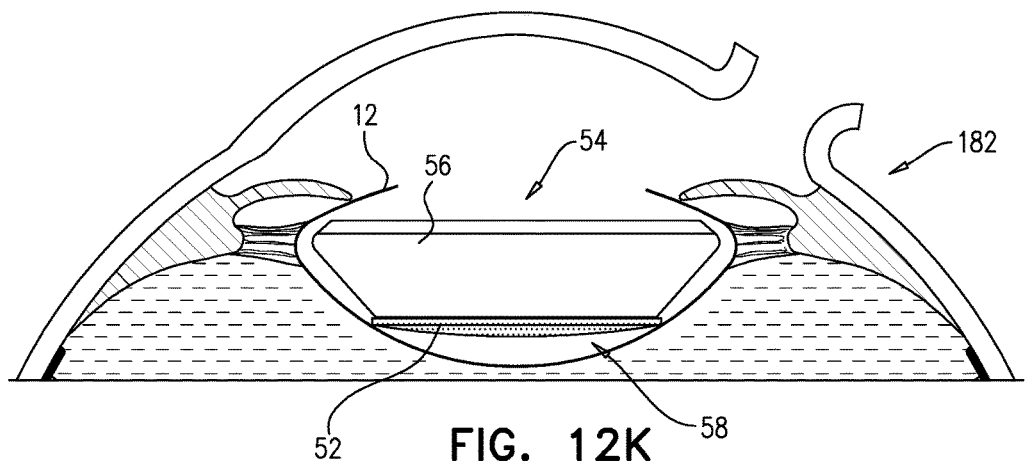
FIG. 12K

ACCOMODATIVE INTRAOCULAR LENS

FIELD OF THE APPLICATION

The present invention relates generally to implantable medical devices, and specifically to intraocular lenses.

BACKGROUND OF THE APPLICATION

Accommodating intraocular lenses (AIOLs) allow the eye to focus at different distances. The Crystalens® (Bausch & Lomb, Rochester, N.Y., USA) is an AIOL that has received FDA approval in the United States.

US Patent Application Publication 2011/0071628 to Gross et al. describes an accommodating intraocular lens (AIOL) implant that includes at least an anterior floating lens complex and a posterior lens complex, each of which comprises one or more optical elements, and a frame comprising one or more levers, which are coupled to the frame and the anterior floating lens complex. The levers are configured to leverage motion of the frame to move the anterior floating lens complex with respect to the posterior lens complex. Other embodiments are also described.

PCT Publication WO 2015/198236 to Sohn et al., which is incorporated herein by reference, describes an accommodating intraocular lens implant that includes an anterior floating lens unit, a posterior lens unit, an anterior rim complex disposed such that the anterior floating lens unit is movable toward and away from the anterior rim complex. A plurality of levers are in jointed connection with: the anterior floating lens unit at respective first longitudinal sites along the levers, the anterior rim complex at respective second longitudinal sites along the levers, and the posterior lens unit at respective third longitudinal sites along the levers. For each of the levers, (a) a line defined by the second and third longitudinal sites, if projected onto a plane defined by a radially-outer perimeter of the lens implant, and (b) a line tangential to the radially-outer perimeter of the lens implant at a circumferential site of the perimeter circumferentially corresponding to the third longitudinal site, form an angle of between 75 and 105 degrees.

SUMMARY OF THE APPLICATION

In some applications of the present invention, an accommodative intraocular lens implant comprises an anterior assembly and a posterior lens unit, which comprises a posterior lens. For some applications, the anterior assembly comprises first and second anterior components. The first anterior component typically comprises exactly one first polymeric piece, which is shaped so as to define levers and an anterior floating lens unit, which comprises an anterior lens. The second anterior component typically comprises exactly one second polymeric piece, and typically is separate and distinct from the first anterior component prior to assembly with the first anterior component. The second anterior component is shaped so as to define an anterior rim complex, and anterior rim links, which are connected to the anterior rim complex. The lens implant is configured such that the distance between the anterior floating lens unit and the posterior lens unit (in the anterior-posterior direction) changes in response to the natural accommodation mechanism of the eye, thereby adjusting the focal length of the lens implant. The levers magnify the relatively small change in the width of the lens implant caused by the natural change in the shape of the natural capsular bag, in order to move the anterior floating lens unit a greater distance with respect to the posterior lens unit. Because of this distance magnification, the lens implant provides a high level of accommodation that mimics that of the natural eye.

The anterior rim complex is disposed such that the anterior floating lens unit is movable toward and away from the anterior rim complex, in the anterior-posterior direction. As the width (in the anterior-posterior direction) of the capsular bag changes, the anterior rim complex moves with respect to the posterior lens unit, thereby changing the distance therebetween.

For some applications, the anterior assembly and the posterior lens unit are distinct from each other and not permanently fixed to each other, and are shaped so as to be assemblable together in situ in the capsular bag of the human eye.

For some applications, the posterior lens unit comprises (a) a first posterior component, which comprises a posterior lens rim, and (b) a second posterior component, which (i) is distinct and separate from the first posterior component, and (ii) comprises the posterior lens. The posterior lens and the posterior lens rim are shaped so as to be assemblable together in situ in the capsular bag such that the posterior lens rim radially surrounds at least an axial portion of the posterior lens.

For some applications, the levers are in jointed connection with (a) the anterior floating lens unit at respective first longitudinal sites along the levers, (b) the anterior rim links, respectively, at respective second longitudinal sites along the levers, and (c) the posterior lens unit at respective third longitudinal sites along the levers.

For some applications, the levers are shaped so as to define respective posterior sides, respective anterior sides, and respective first and second lateral sides. The anterior rim links are shaped so as to define (a) respective lever-contact surfaces, which are shaped and disposed so as to pivotably engage respective anterior sides of the levers at respective second longitudinal sites along the levers, and (b) respective first and second side arms, which extend more posteriorly than the respective lever-contact surfaces. The first side arms are disposed at least partially alongside respective the first lateral sides of respective levers, and the second side arms are disposed at least partially alongside the respective second lateral sides of the respective levers.

For some applications, the anterior floating lens unit further comprises (a) an anterior lens ring, which has a diameter greater than that of the anterior lens, and (b) rim-connector elements, which are distributed around the anterior lens ring at respective connector sites, and connect the anterior lens ring to the anterior lens such that the anterior lens ring does not directly contact the anterior lens. The levers are connected to the respective lever-ring sites around the anterior lens ring, at the respective first longitudinal sites along the levers. Typically, the connector sites are circumferentially offset from the lever-ring sites. For example, each of the lever-ring sites may be circumferentially centered between two circumferentially-adjacent ones of the connector sites. For some applications, the accommodating intraocular lens implant is configured such that the anterior lens ring deforms during a transition of accommodating intraocular lens implant between the fully-accommodated state and the fully-unaccommodated state.

The lens implant's accommodation typically provides a continuous range of focus, including near, distance, and intermediate distances. The lens implant exploits the natural accommodation mechanism of the eye, which reacts in order to sharpen the image on the retina. The lens implant thus typically reduces the need for glasses, which are generally required by patients with conventional IOLs. The lens implant is typically implanted in the eye after natural lens removal because of cataract, or for Refractive Lens Exchange (RLE), using well-known IOL implantation techniques, including making a small incision.

There is therefore provided, in accordance with an application of the present invention, apparatus including an accommodating intraocular lens implant, which includes:

(a) an anterior assembly, which includes:
a first anterior component, which includes exactly one first polymeric piece, which is shaped so as to define (i) an anterior floating lens unit, which includes an anterior lens, and (ii) levers; and
a second anterior component, which (a) includes exactly one second polymeric piece, (b) is assembled with the first anterior component such that the first and the second anterior components are separable from each other without tearing the first anterior component and without tearing the second anterior component, and (c) is shaped so as to define (i) an anterior rim complex, and (ii) anterior rim links, which are connected to the anterior rim complex; and (b) a posterior lens unit, which includes a posterior lens, wherein the levers are (a) in jointed connection with the anterior floating lens unit at respective first longitudinal sites along the levers, (b) in jointed and interlocked connection with the anterior rim links, respectively, at respective second longitudinal sites along the levers, (c) in jointed connection with the posterior lens unit at respective third longitudinal sites along the levers, and (d) arranged to move the anterior floating lens unit toward and away from the anterior rim complex, in an anterior-posterior direction, and wherein, for each respective lever of the levers, the second longitudinal site is longitudinally between the first and the third longitudinal sites along the respective lever, such that the third longitudinal site serves as a fulcrum for the respective lever.

For some applications, the anterior assembly and the posterior lens unit are distinct from each other and not permanently fixed to each other, and are shaped so as to be assemblable together in situ in a capsular bag of a human eye.

For some applications, the third longitudinal sites are at respective end-most sites of the respective levers.

For some applications, the respective third longitudinal sites along the levers directly contact the posterior lens unit.

For some applications, for each respective lever of the levers, (a) a straight line defined by the first longitudinal site of the respective lever and the third longitudinal site of the respective lever, when projected onto a plane defined by a radially-outer perimeter of the accommodating intraocular lens implant, and (b) a straight line that is in the plane and that is tangential to the radially-outer perimeter of the accommodating intraocular lens implant at a circumferential site of the radially-outer perimeter circumferentially corresponding to the third longitudinal site of the respective lever, form an angle of between 75 and 105 degrees.

For some applications:
the levers are shaped so as to define respective posterior sides, respective anterior sides, and respective first and second lateral sides,
the anterior rim links are shaped so as to define:
(a) respective lever-contact surfaces, which are shaped and disposed so as to pivotably engage the respective anterior sides of the levers at the respective second longitudinal sites along the levers, and (b) respective first and second side arms, which extend more posteriorly than the respective lever-contact surfaces, and
the first side arms are disposed at least partially alongside the respective first lateral sides of the respective levers, and
the second side arms are disposed at least partially alongside the respective second lateral sides of the respective levers.

For some applications, the anterior rim links are shaped so as to define respective posterior end pieces, which link the respective first side arms to the respective second side arms posteriorly beyond the respective first and second lateral sides. For some applications, the posterior sides of the levers are convexly curved at least along 0.2 mm of the respective levers longitudinally surrounding the respective second longitudinal sites. For some applications, respective convexly-curved portions of the posterior sides of the respective levers are concentric with the respective second longitudinal sites of the respective levers.

For some applications, the posterior end pieces do not come in contact with the respective posterior sides of the respect levers at any point during a transition of the accommodating intraocular lens implant between a fully-accommodated state and a fully-unaccommodated state. For some applications, the posterior sides of the levers are convexly curved at least along 0.2 mm of the respective levers longitudinally surrounding the respective second longitudinal sites. For some applications, respective convexly-curved portions of the posterior sides of the respective levers are concentric with the respective second longitudinal sites of the respective levers.

For some applications, the levers are shaped so as to define respective indentations on respective anterior sides at the respective second longitudinal sites, and the anterior rim links are shaped and disposed so as to pivotably engage the respective indentations.

For some applications, the anterior floating lens unit further includes an anterior lens ring, which has a diameter greater than that of the anterior lens; and rim-connector elements, which are distributed around the anterior lens ring at respective connector sites, and connect the anterior lens ring to the anterior lens such that the anterior lens ring does not directly contact the anterior lens, and the levers are connected to respective lever-ring sites around the anterior lens ring, at the respective first longitudinal sites along the levers. For some applications, the connector sites are circumferentially offset from the lever-ring sites. For some applications, each of the lever-ring sites is circumferentially centered between two circumferentially-adjacent ones of the connector sites. For some applications, the accommodating intraocular lens implant is configured such that the anterior lens ring deforms during a transition of the accommodating intraocular lens implant between a fully-accommodated state and a fully-unaccommodated state.

For some applications, the anterior lens ring has a circular longitudinal axis around the anterior lens ring, and the accommodating intraocular lens implant is configured such that the anterior lens ring locally twists around the circular longitudinal axis during the transition of the accommodating intraocular lens implant between the fully-accommodated state and the fully-unaccommodated state.

For some applications, the first polymeric piece includes acrylic. For some applications, the second polymeric piece includes acrylic There is further provided, in accordance with an application of the present invention, apparatus including an accommodating intraocular lens implant, which includes:

an anterior floating lens unit, which includes:
(a) an anterior lens;
(b) an anterior lens ring, which has a diameter greater than that of the anterior lens; and
(c) rim-connector elements, which are distributed around the anterior lens ring at respective connector sites, and connect the anterior lens ring to the anterior lens such that the anterior lens ring does not directly contact the anterior lens;
an anterior rim complex;
anterior rim links, which are connected to the anterior rim complex;
a posterior lens unit, which includes a posterior lens; and
levers, which are (a) in jointed connection with (i) respective lever-ring sites around the anterior lens ring at respective first longitudinal sites along the levers, (ii) the anterior rim links, respectively, at respective second longitudinal sites along the levers, and (iii) the posterior lens unit at respective third longitudinal sites along the levers, and (b) are arranged to move the anterior floating lens unit toward and away from the anterior rim complex, in an anterior-posterior direction,
wherein, for each respective lever of the levers, the second longitudinal site is longitudinally between the first and the third longitudinal sites along the respective lever, such that the third longitudinal site serves as a fulcrum for the respective lever.

For some applications, the connector sites are circumferentially offset from the lever-ring sites. For some applications, each of the lever-ring sites is circumferentially centered between two circumferentially-adjacent ones of the connector sites.

For some applications, the accommodating intraocular lens implant is configured such that the anterior lens ring deforms during a transition of the accommodating intraocular lens implant between a fully-accommodated state and a fully-unaccommodated state. For some applications, the anterior lens ring has a circular longitudinal axis around the anterior lens ring, and the accommodating intraocular lens implant is configured such that the anterior lens ring locally twists around the circular longitudinal axis during the transition of the accommodating intraocular lens implant between the fully-accommodated state and the fully-unaccommodated state.

There is still further provided, in accordance with an application of the present invention, apparatus including:
(a) an accommodating intraocular lens implant, which includes:
  (i) an anterior floating lens unit, which includes an anterior lens;
  (ii) a first posterior component, which includes a posterior lens rim; and
  (iii) a second posterior component, which (A) is distinct and separate from the first posterior component prior to assembly with the first posterior component, and (B) includes a posterior lens,
  wherein the first and the second posterior components are shaped so as to be assemblable together in situ in a capsular bag of a human eye such that the posterior lens rim radially surrounds at least an axial portion of the posterior lens, and
  wherein, when the first and the second posterior components are assembled together, the first and the second posterior components are separable from each other without tearing the first posterior component and without tearing the second posterior component; and
(b) an introducer tube, in which the posterior lens rim is removably disposed while folded or rolled.

For some applications:
the posterior lens rim, when in an unconstrained state, includes a frustoconical portion and defines larger and smaller openings,
the posterior lens is insertable into and coupleable with the smaller opening, and
the posterior lens rim is removably disposed in the introducer tube while the posterior lens rim is inverted from its unconstrained state and folded or rolled.

For some applications, the posterior lens rim, when in the unconstrained state, is shaped so as to define a convex posterior surface.

For some applications, the posterior lens rim is removably disposed in the introducer tube while folded in half.

For some applications:
the posterior lens rim, when in an unconstrained state, is shaped as a partial bowl surrounding an opening into which the posterior lens is insertable, and
the posterior lens rim is removably disposed in the introducer tube while the bowl is inverted from its unconstrained state and folded in half.

For some applications, the posterior lens rim is removably disposed in the introducer tube while folded in quarters.

For some applications:
the posterior lens rim, when in an unconstrained state, is shaped as a partial bowl surrounding an opening into which the posterior lens is insertable, and
the posterior lens rim is removably disposed in the introducer tube while the bowl is inverted from its unconstrained state and folded in quarters.

For some applications, the posterior lens rim includes acrylic.

There is additionally provided, in accordance with an application of the present invention, a method including:
providing an accommodating intraocular lens implant, which includes:
(a) an anterior assembly, which includes:
  a first anterior component, which includes exactly one first polymeric piece, which is shaped so as to define (i) an anterior floating lens unit, which includes an anterior lens, and (ii) levers; and
  a second anterior component, which (a) includes exactly one second polymeric piece, (b) is assembled with the first anterior component such that the second anterior component is separable from the first anterior component without tearing the first anterior component and without tearing the second anterior component, and (c) is shaped so as to define (i) an anterior rim complex, and (ii) anterior rim links, which are connected to the anterior rim complex; and
(b) a posterior lens unit, which includes a posterior lens,
  wherein the levers are (a) in jointed connection with the anterior floating lens unit at respective first longitudinal sites along the levers, (b) in jointed and interlocked connection with the anterior rim links, respectively, at respective second longitudinal sites along the levers, (c) in jointed connection with the posterior lens unit at respective third longitudinal sites along the levers, and (d) arranged to move the anterior floating lens unit toward and away from the anterior rim complex, in an anterior-posterior direction, and
  wherein, for each respective lever of the levers, the second longitudinal site is longitudinally between the first and the third longitudinal sites along the respective lever, such that the third longitudinal site serves as a fulcrum for the respective lever; and implanting the accommodating intraocular lens implant in a natural capsular bag of a patient.

There is yet additionally provided, in accordance with an application of the present invention, a method including:

providing an accommodating intraocular lens implant, which includes:
an anterior floating lens unit, which includes:
(a) an anterior lens;
(b) an anterior lens ring, which has a diameter greater than that of the anterior lens; and
(c) rim-connector elements, which are distributed around the anterior lens ring at respective connector sites, and connect the anterior lens ring to the anterior lens such that the anterior lens ring does not directly contact
the anterior lens;
an anterior rim complex;
anterior rim links, which are connected to the anterior rim complex;
a posterior lens unit, which includes a posterior lens; and
levers, which are (a) in jointed connection with (i) respective lever-ring sites around the anterior lens ring at respective first longitudinal sites along the levers, (ii) the anterior rim links, respectively, at respective second longitudinal sites along the levers, and (iii) the posterior lens unit at respective third longitudinal sites along the levers, and (b) are arranged to move the anterior floating lens unit toward and away from the anterior rim complex, in an anterior-posterior direction,
wherein, for each respective lever of the levers, the second longitudinal site is longitudinally between the first and the third longitudinal sites along the respective lever, such that the third longitudinal site serves as a fulcrum for the respective lever; and implanting the accommodating intraocular lens implant in a natural capsular bag of a patient.

There is also provided, in accordance with an application of the present invention, a method including:

providing an introducer tube in which a posterior lens rim of a first posterior component of an accommodating intraocular lens implant is removably disposed while folded or rolled;

inserting the introducer tube into a capsular bag of a human eye;

releasing the posterior lens rim from the introducer tube in the capsular bag, and allowing the posterior lens rim to unfold or unroll in the capsular bag;

inserting, into the capsular bag, a posterior lens of a second posterior component, while the second posterior component is separate and distinct from the first posterior component;

thereafter, assembling together the posterior lens and the posterior lens rim in situ in the capsular bag such that the posterior lens rim radially surrounds at least an axial portion of the posterior lens; and thereafter, inserting, into the capsular bag, an anterior lens of an anterior floating lens unit, and coupling the anterior floating lens unit to the second posterior component.

For some applications, inserting the posterior lens into the capsular bag includes inserting the posterior lens into the capsular bag after releasing the posterior lens rim from the introducer tube in the capsular bag. For other applications, inserting the posterior lens into the capsular bag includes inserting the posterior lens into the capsular bag before releasing the posterior lens rim from the introducer tube in the capsular bag.

For some applications:
the posterior lens rim, when in an unconstrained state, includes a frustoconical portion and defines larger and smaller openings,
the posterior lens is insertable into and coupleable with the smaller opening, and
providing the introducer tube includes providing the introducer tube in which the posterior lens rim is removably disposed while the posterior lens rim is inverted from its unconstrained state and folded or rolled.

For some applications, the posterior lens rim, when in the unconstrained state, is shaped so as to define a convex posterior surface.

For some applications, providing the introducer tube includes providing the introducer tube in which the posterior lens rim is removably disposed while folded in half.

For some applications:
the posterior lens rim, when in an unconstrained state, is shaped as a partial bowl surrounding an opening into which the posterior lens is insertable, and
providing the introducer tube includes providing the introducer tube in which the posterior lens rim is removably disposed while the bowl is inverted from its unconstrained state and folded in half.

For some applications, providing the introducer tube includes providing the introducer tube in which the posterior lens rim is removably disposed while folded in quarters.

For some applications:
the posterior lens rim, when in an unconstrained state, is shaped as a partial bowl surrounding an opening into which the posterior lens is insertable, and
providing the introducer tube includes providing the introducer tube in which the posterior lens rim is removably disposed while the bowl is inverted from its unconstrained state and folded in quarters.

For some applications, the posterior lens rim includes acrylic.

The present invention will be more fully understood from the following detailed description of embodiments thereof, taken together with the drawings, in which:

BRIEF DESCRIPTION OF THE DRAWINGS

FIGS. 2A-C are schematic illustrations of the accommodative intraocular lens implant of FIGS. 1A-C implanted in a natural capsular bag of the eye, in accordance with an application of the present invention;

FIGS. 3A-B are schematic illustration of components of the lens implant of FIGS. 1A-C and 2A-C prior to assembly and after assembly, respectively, in accordance with an application of the present invention;

FIGS. 4A-B are schematic cross-sectional illustrations of the lens implant of FIGS. 1A-C and 2A-C in a fully-unaccommodated state and a fully-accommodated state, respectively, in accordance with an application of the present invention;

FIG. 5A-C are schematic illustrations of one lever and one anterior rim link of the lens implant of FIGS. 1A-C and 2A-C, in accordance with an application of the present invention;

FIG. 6 is a schematic illustration of another configuration of one anterior rim link of the lens implant of FIGS. 1A-C and 2A-C, in accordance with an application of the present invention;

FIG. 11 is a schematic illustration of the removable disposal of an anterior assembly of the lens implant of FIGS. 1A-C and 2A-C in a third introducer tube, in accordance with an application of the present invention; and FIGS. 12A-M are schematic illustrations of a method of implanting the lens implant of FIGS. 1A-C and 2A-C, in accordance with an application of the present invention.

DETAILED DESCRIPTION OF APPLICATIONS

Figure 1A:
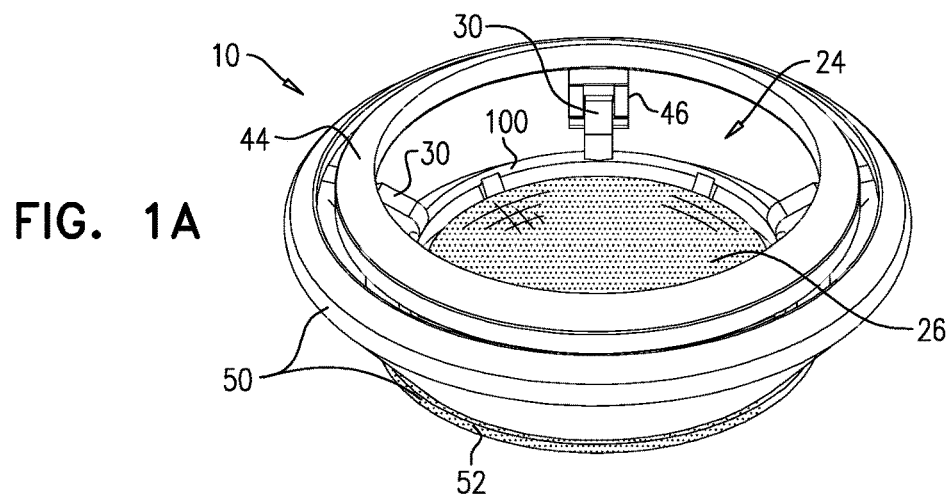
FIGS. 1A-C are schematic illustrations of an accommodative intraocular lens implant, in accordance with an application of the present invention.
Figure 1B:
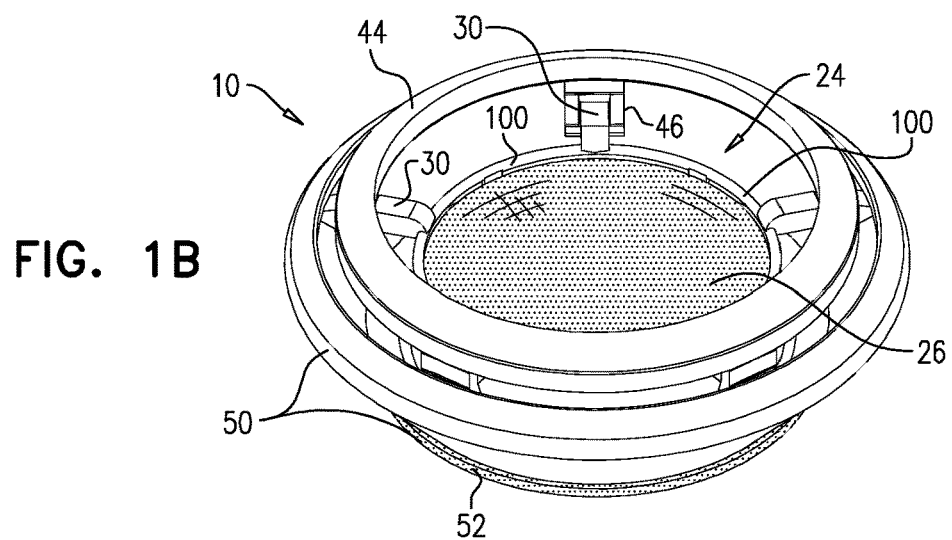
Figure 1C:
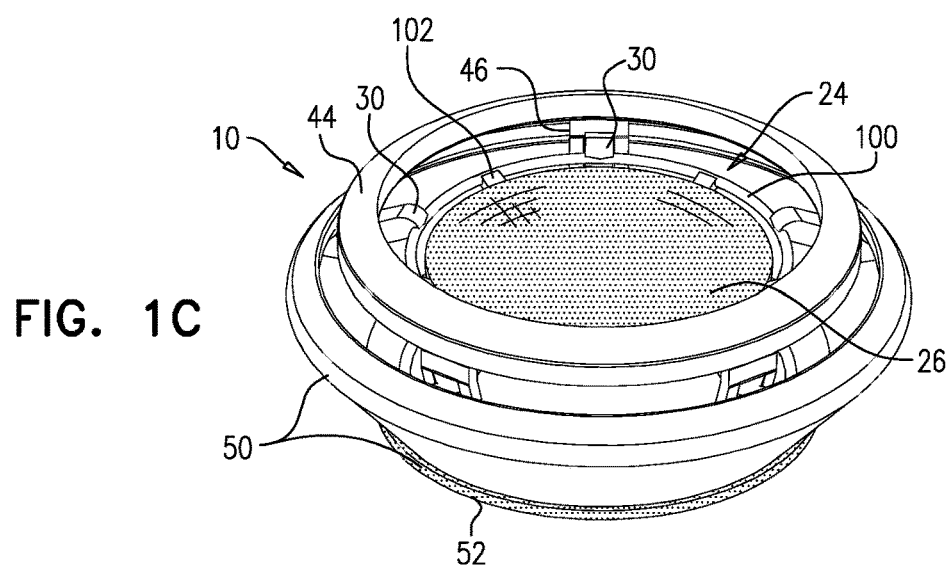

FIGS. 1A-C and 2A-C are schematic illustrations of an accommodative intraocular lens implant 10, in accordance with an application of the present invention. FIGS. 1A-C are isometric views of the lens implant. FIGS. 2A-C are side views showing the lens implant implanted in a natural capsular bag 12 of the eye. FIGS. 1A and 2A show lens implant 10 in a fully-unaccommodated state, FIGS. 1B and 2B show lens implant 10 in a partially-accommodated state, and FIGS. 1C and 2C show the lens implant in a fully-accommodated state. Although only these three states are shown in these and some of the other figures, lens implant 10 is configured to assume a continuous range of accommodation between the fully-unaccommodated state and the fully-accommodated state. The fully-accommodated state provides near vision, the fully-unaccommodated state provides distance vision, and partially-accommodated states therebetween provide intermediate vision. The lens implant is configured to reach the fully-accommodated state responsively to the natural accommodation mechanism of the eye, without the need for external power. The resting state of the lens implant is typically the fully-accommodated state, or, optionally, slightly beyond the fully-accommodated state, such that the lens implant is always pressing the lens capsule open even when the lens implant is fully accommodated, thereby keeping the zonules in tension.

Reference is still made to FIGS. 1A-C and 2A-C, and is additionally made to FIGS. 3A-B, which are schematic illustration of components of lens implant 10 prior to assembly and after assembly, respectively, in accordance with an application of the present invention.

Lens implant 10 comprises (a) an anterior assembly 18 and (b) a posterior lens unit 50, which comprises a posterior lens 52. For some applications, anterior assembly 18 comprises:

a first anterior component 20, which typically comprises exactly one first polymeric piece 22, which is shaped so as to define (i) an anterior floating lens unit 24, which comprises an anterior lens 26, and (ii) levers 30; and a second anterior component 40, which (a) typically comprises exactly one second polymeric piece 42, (b) typically is separate and distinct from first anterior component 20 prior to assembly with first anterior component 20, and (c) is shaped so as to define (i) an anterior rim complex 44, and (ii) anterior rim links 46, which are connected to anterior rim complex 44.

Typically, first and second anterior components 20 and 40 are assembled together during the manufacturing process. Because first and second anterior components 20 and 40 are separate and distinct from each other prior to assembly together, first and second anterior components 20 and 40 are separable from each other without tearing first anterior component 20 and without tearing second anterior component 40. For some applications, first and second polymeric pieces 22 and 24 are manufactured by injection molding. First and second polymeric pieces 22 and 24 may be more readily molded as separate pieces that are later assembled together during manufacture.

As appropriate, lens implant 10 may partially or wholly comprise silicone, or lens implant 10 may partially or wholly comprise acrylic. For some applications, a portion of lens implant 10 comprises silicone and another portion of lens implant 10 comprises acrylic (optionally, lens implant 10 consists essentially entirely of silicone and acrylic).

For some applications, posterior lens rim 56 comprises acrylic, which is typically flexible, any may be either hydrophobic or hydrophilic. Acrylic has shape memory, like silicone, but acrylic returns to its memorized shape more slowly than silicone, which provides more control during the implantation procedure than does silicone. Alternatively or additionally, first polymeric piece 22 comprises acrylic, and/or second polymeric piece 42 comprises acrylic.

It is noted that having lens implant 10 comprise acrylic (e.g., by consisting essentially entirely of acrylic) solves problems associated with use of silicone, such as "flash" (silicone leakage during injection molding). Even known flashless silicone molding techniques pose technical challenges when utilized with mold shapes that are complex. In addition, since suitable acrylic has a refractive index of up to about 1.52, while a suitable commercially-available silicone has a refractive index of 1.43, use of an acrylic lens as anterior lens 26 allows anterior lens 26 to be smaller than if anterior lens 26 were to comprise silicone; the same benefit may be achieved by posterior lens 52 if it comprises acrylic.

For some applications, (a) the material of first polymeric piece 22 has a hardness of between 20 and 70 Shore A, (b) the material of second polymeric piece 42 has a hardness of between 20 and 70 Shore A, (c) the material of first posterior component 54 has a hardness of between 20 and 70 Shore A, and (d) the material of a second posterior component 58 has a hardness of between 20 and 70 Shore A. Thus, all components of lens implant 10 are typically flexible.

For some applications, anterior assembly 18 and posterior lens unit 50 are distinct from each other and not permanently fixed to each other, and are shaped so as to be assemblable together in situ in capsular bag 12 of a human eye.

For some applications, lens implant 10 comprises between three and eight levers 30, such as three, four, five, or six levers 30, and a corresponding number of anterior rim links 46.

For some applications, posterior lens unit 50 comprises (a) a first posterior component 54, which comprises a posterior lens rim 56, and (b) a second posterior component 58, which (i) is distinct and separate from first posterior component 54, and (ii) comprises posterior lens 52. Because first and second posterior components 54 and 58 are separate and distinct from each other prior to assembly together, first and second posterior components 54 and 58 are separable from each other without tearing first posterior component 54 and without tearing second posterior component 58. As described hereinbelow with reference to FIGS. 12F and 12G, posterior lens 52 and posterior lens rim 56 are shaped so as to be assemblable together in situ in capsular bag 12 of a human eye such that posterior lens rim 56 radially surrounds at least an axial portion 59 of posterior lens 52 (labeled in FIG. 4A). (As used in the present application, including in the claims, "axial" means a direction along a central optical axis of lens implant 10. As used in the present application, including in the claims, "radial" means in a direction toward or away from the central optical axis of lens implant 10.) (Although transparent, anterior lens 26 and posterior lens 52 are shaded in the figures for clarity of illustration; the lenses may comprise the same material as some or all the other components of the lens implant.)

Posterior lens unit 50 remains generally motionless with respect to the posterior portion of natural capsular bag 12 of the eye during accommodation of lens implant 10. Lens implant 10 is configured such that anterior floating lens unit 24 moves with respect to posterior lens unit 50 in response to the natural accommodation mechanism of the eye. The natural accommodation mechanism of the eye changes the shape of natural capsular bag 12, as shown in FIGS. 2A-C. In the fully-unaccommodated state shown in FIG. 2A, the ciliary muscle is relaxed and the zonular fibers are therefore tensed, causing the capsular bag to assume a relatively narrow width (in an anterior-posterior direction) and relatively large diameter. Thus shaped, the capsular bag squeezes the lens implant in the anterior-posterior direction. In contrast, in the fully-accommodated state shown in FIG. 2C, the ciliary muscle contracts, thereby releasing the tension of the zonular fibers on the capsular bag, causing the capsular bag to assume a relatively large width and relative small diameter. This shape of the capsular bag allows the lens implant to expand in the anterior-posterior direction. (As used herein, the diameter of the capsular bag means the greatest diameter of the capsular bag when viewed from its posterior aspect.)

Anterior rim complex 44 is disposed such that anterior floating lens unit 24 is movable toward and away from anterior rim complex 44, in the anterior-posterior direction. As the width (in the anterior-posterior direction) of the capsular bag changes, anterior rim complex 44 moves with respect to posterior lens unit 50, thereby changing the distance therebetween.

As mentioned above, anterior floating lens unit 24 comprises anterior lens 26, and posterior lens unit 50 comprises posterior lens 52. Each of lens units 24 and 50 may comprise one or more additional optical elements, such as additional lenses (e.g., convex lenses, concave lenses, biconvex lenses, biconcave lenses, spherical lenses, aspheric lenses, and/or astigmatic lenses), fixed power optics, deformable optics, aberration free optics, doublets, triplets, filtered optics, or combinations of these lenses, as is known in the optical arts. For some applications, anterior lens 26 is the only optical element of anterior floating lens unit 24, and/or posterior lens 52 is the only optical element of posterior lens unit 50. For some applications, one or more of lens units 24 and 50 are attached to the implant during manufacture. Alternatively or additionally, one or more of the lens units may be attached by a healthcare worker either prior to or during the implantation procedure, such as to provide the lens unit most appropriate for the particular patient.

Reference is now made to FIGS. 4A-B, which are schematic cross-sectional illustrations of lens implant 10 in the fully-unaccommodated state and the fully-accommodated state, respectively, in accordance with an application of the present invention. Levers 30 are arranged to move anterior floating lens unit 24 toward and away from anterior rim complex 44, in an anterior-posterior direction. Levers 30 are:

in jointed connection with anterior floating lens unit 24 at respective first longitudinal sites 60 along levers 30, in jointed and interlocked connection with anterior rim links 46, respectively, at respective second longitudinal sites 62 along levers 30, and in jointed connection with posterior lens unit 50 at respective third longitudinal sites 64 along levers 30.

As used in the present application, including in the claims, a "lever" is a beam that is used to move an object at a first point by a force applied at a second point, and that pivots about a fulcrum at a third point. For each respective lever 30 of levers 30, the second longitudinal site 62 is longitudinally between first longitudinal site 60 and third longitudinal site 64 along the respective lever 30, such that third longitudinal site 64 serves as a fulcrum 66 for respective lever 30. Thus, first longitudinal site 60, second longitudinal site 62, and third longitudinal site 64 correspond with the first, second, and third points, respectively, in the definition above. Typically anterior rim links 46 pivot with reference to respective levers 30. Typically, during accommodation of lens implant 10 in the patient's eye, levers 30 and anterior rim links 46 do not bend or deform, but instead move with respect to each other. Typically, levers 30 are in interlocked connection with anterior rim links 46.

For some applications, third longitudinal sites 64 are at respective end-most sites 68 of respective levers 30. (The phrase "along" lever 30 is to be understood as including the ends of the lever; for example, third longitudinal site 64 may be at one end of the lever, as shown.) For some applications, each of levers 30 is in jointed connection with posterior lens unit 50 at an end-most site of the lever 30, when posterior lens unit 50 and first anterior component 20 are assembled together, typically in situ. Alternatively or additionally, for some applications, respective third longitudinal sites 64 along levers 30 directly contact posterior lens unit 50.

Force is applied to second longitudinal site 62 by anterior rim complex 44, and, as a result, first longitudinal site 60 (and anterior floating lens unit 24) moves more than an anterior-posterior distance that second longitudinal site 62 (and anterior rim complex 44) moves, typically between 1.5 and 4 times the anterior-posterior distance that second longitudinal site 62 (and anterior rim complex 44) moves. For some applications, a distance between second and third longitudinal sites 62 and 64 is between 0.8 and 1.6 mm, and a distance between first and third longitudinal sites 60 and 64 is between 1.2 and 2.4 mm, providing a gain of between 1.5 and 4. Typically, second longitudinal sites 62 are disposed radially inward from third longitudinal sites 64, respectively. Typically, first longitudinal sites 60 are disposed radially inward from second longitudinal sites 62 and third longitudinal sites 64, respectively.

Levers 30 are thus configured to magnify the relatively small change in the distance between anterior rim complex 44 and posterior lens unit 50, in order to move anterior floating lens unit 24 by a greater distance with respect to posterior lens unit 50. In other words, lens implant 10 is configured such that levers 30 move anterior floating lens unit 24 by a first anterior-posterior distance with respect to posterior lens unit 50 when anterior rim complex 44 moves a second anterior-posterior distance with respect to posterior lens unit 50, which first distance is greater than the second distance. Because of this distance magnification, the lens implant provides a high level of accommodation that mimics that of the natural eye. Typically, the first distance is at least 1.4 times the second distance, i.e., the lever provides a gain of at least 1.4. For example, the first distance may be at least 1.5 (e.g., at least 1.8, such as between 1.8 and 3) times the second distance.

The anterior and posterior movement of anterior floating lens unit 24 changes the distance between the anterior and posterior lens units, thereby adjusting the focal length of the lens implant. In the fully-accommodated state, which provides near vision, lens implant 10 is relatively wide (in the anterior-posterior direction), with a large separation between the anterior and posterior lens units, creating a large free space between the complexes. In the fully-unaccommodated state, which provides distance vision, the implant is relatively narrow, with a small separation between anterior and posterior complexes. Anterior floating lens unit 24 typically shifts at least 1 mm between the fully-unaccommodated and fully-accommodated states. Typical movement of the anterior lens relative to the posterior lens is between 0.5 and 2.0 mm, such as between 1 and 1.5 mm, as the lens implant transitions between the fully-unaccommodated and fully-accommodated states.

Anterior floating lens unit 24 moves within an interior space of lens implant 10, which is typically open to the natural fluid within the eye. The floating lens unit is configured to create minimum drag during movement, while maintaining the optical performance of the combined lens structure. For example, the floating lens unit may have a smooth shape, and/or may be coated with a hydrophobic coating such as silicone. Typically, the anterior and posterior lens units are configured to together create an optical structure having a total power that varies between +15D and +25D, as selected by the physician implanting the lens implant.

To minimize posterior capsular opacification, posterior lens 52 is typically provided with a clearly-defined corner 99 (e.g., having an angle of 80-150 degrees, e.g., 90-120 degrees), at the junction of the posterior and lateral surfaces of posterior lens 52.

Reference is now made to FIG. 5A-C, which are schematic illustrations of one lever 30 and one anterior rim link 46, in accordance with an application of the present invention. FIG. 5A shows lever 30, FIG. 5B shows anterior rim link 46, and FIG. 5C shows anterior rim link 46 coupled to lever 30. For some applications, levers 30 are shaped so as to define respective posterior sides 80, respective anterior sides 82, and respective first and second lateral sides 84A and 84B (second lateral side 84B is not visible in FIGS. 5A and 5C). Anterior rim links 46 are shaped so as to define:
  respective lever-contact surfaces 86, which are shaped and disposed so as to pivotably engage respective anterior sides 82 of levers 30 at respective second longitudinal sites 62 along levers 30, and
  respective first and second side arms 88A and 88B, which extend more posteriorly than respective lever-contact surfaces 86.
First side arms 88A are disposed at least partially alongside respective first lateral sides 84A of respective levers 30, and second side arms 88B are disposed at least partially alongside respective second lateral sides 84B of respective levers 30.

For some applications, such as shown in FIGS. 5B-C, anterior rim links 46 are shaped so as to define respective posterior end pieces 90, which link respective first side arms 88A to respective second side arms 88B posteriorly beyond respective first and second lateral sides 84A and 84B. Typically, posterior end pieces 90 do not come in contact with respective posterior sides 80 of the respect levers at any point during a transition of accommodating intraocular lens implant 10 between the fully-accommodated state and the fully-unaccommodated state. Nevertheless, posterior end pieces 90 may still be provided, such as in order to hold anterior rim links 46 coupled to levers 30 during storage and implantation of first anterior component 20. For some applications, posterior sides 80 of levers 30 are convexly curved at least along 0.2 mm (e.g., at least along 0.3 mm) of respective levers 30 longitudinally surrounding respective second longitudinal sites 62. For some applications, respective convexly-curved portions 92 of posterior sides 80 of respective levers 30 are concentric with respective second longitudinal sites 62 of respective levers 30.

(As used in the present application, including in the claims, transitioning between the fully-accommodated and the fully-unaccommodated states is to be understood as meaning making a transition that begins at the fully-accommodated state and continues all the way to the fully-unaccommodated state, or vice versa.)

For some applications, levers 30 are shaped so as to define respective indentations 96 on respective anterior sides 82 at respective second longitudinal sites 62, and anterior rim links 46 are shaped and disposed so as to pivotably engage respective indentations 96.

Reference is now made to FIG. 6, which is a schematic illustration of another configuration of one anterior rim link 46, in accordance with an application of the present invention. In this configuration, anterior rim links 46 are not shaped so as to define respective posterior end pieces 90. (Nevertheless, levers 30 are still in interlocked connection with anterior rim links 46.)

Reference is made to FIGS. 5A-B and 6. As described hereinabove, lens implant 10 may comprise acrylic, in whole or in part. A technical problem associated with using acrylic rather than silicone is that acrylic is less elastic than silicone, and therefore is liable to break if it undergoes local deformations that may be experienced during the transition between the fully-accommodated and the fully-unaccommodated states. In this regard, lens implant 10 (and particularly the interaction of lever 30 and anterior rim link 46 as shown in FIGS. 5A-B and 6) addresses the technical challenge of creating lens implant 10 using acrylic, by providing lever 30 and anterior rim link 46 formed by molding as separate pieces that are later assembled together during manufacture. Thus, lever-contact surface 86 and anterior side 82 of lever 30 pivot with respect to each other to facilitate the desired transition between the fully-accommodated and the fully-unaccommodated states, substantially without bending of lever-contact surface 86 and/or anterior side 82 of lever 30.

Figure 7:
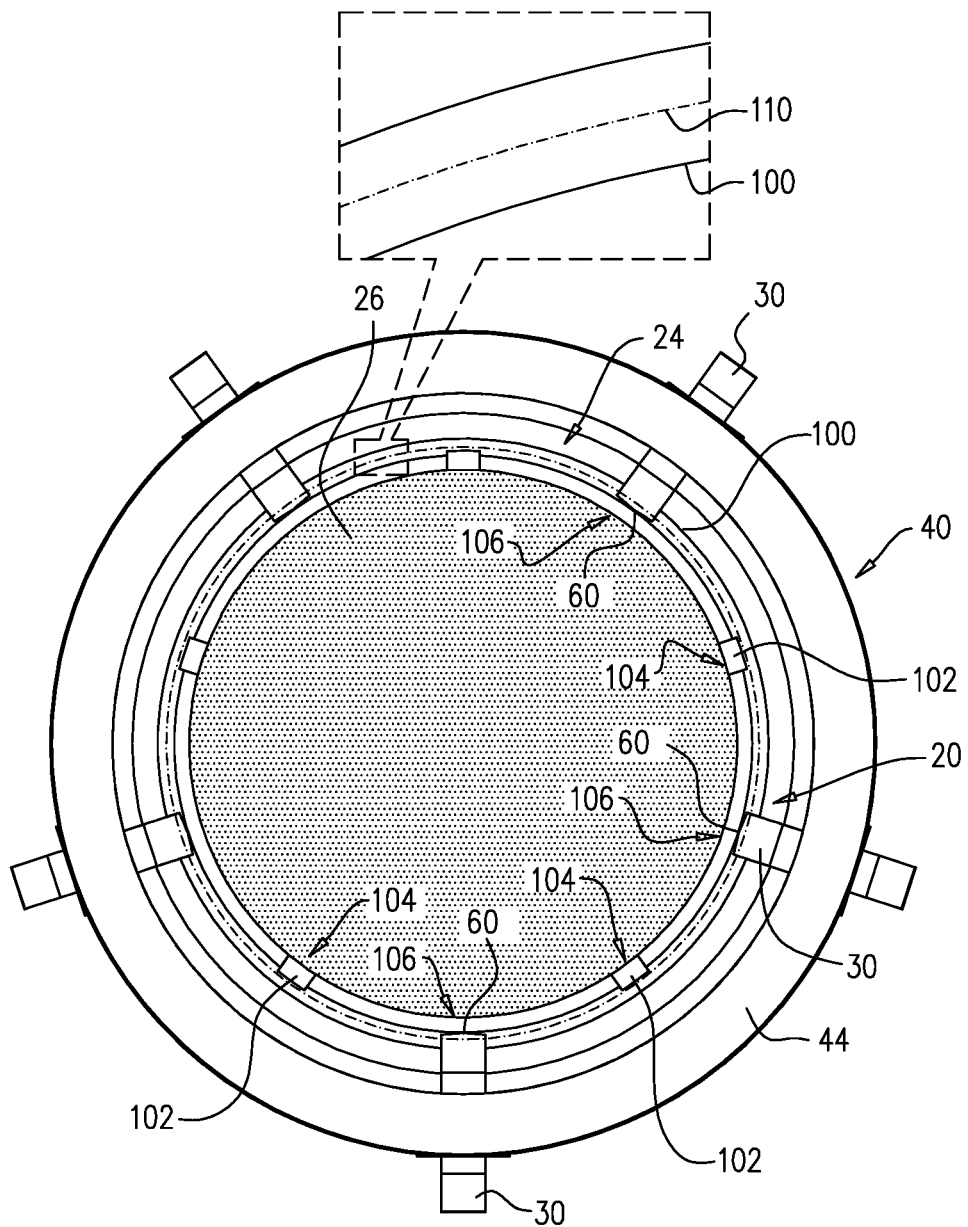
FIG. 7 is a schematic anterior view of first and second anterior components of the lens implant of FIGS. 1A-C and 2A-C, in accordance with an application of the present invention.

Reference is now made to FIG. 7, which is a schematic anterior view of first and second anterior components 20 and 40 of lens implant 10, in accordance with an application of the present invention. For some applications, anterior floating lens unit 24 further comprises:
  an anterior lens ring 100, which has a diameter greater than that of anterior lens 26; and
  rim-connector elements 102, which are distributed around anterior lens ring 100 at respective connector sites 104, and connect anterior lens ring 100 to anterior lens 26 such that anterior lens ring 100 does not directly contact anterior lens 26.

Levers 30 are connected to respective lever-ring sites 106 around anterior lens ring 100, at respective first longitudinal sites 60 along levers 30. Typically, connector sites 104 are circumferentially offset from lever-ring sites 106. For example, each of lever-ring sites 106 may be circumferentially centered between two circumferentially-adjacent ones of connector sites 104, such as shown.

For some applications, accommodating intraocular lens implant 10 is configured such that anterior lens ring 100 deforms during a transition of accommodating intraocular lens implant 10 between the fully-accommodated state and the fully-unaccommodated state. For some applications, anterior lens ring 100 has a circular longitudinal axis 110 around the anterior lens ring, and accommodating intraocular lens implant 10 is configured such that anterior lens ring 100 locally twists around circular longitudinal axis 110 during the transition of accommodating intraocular lens implant 10 between the fully-accommodated state and the fully-unaccommodated state.

Figure 8:
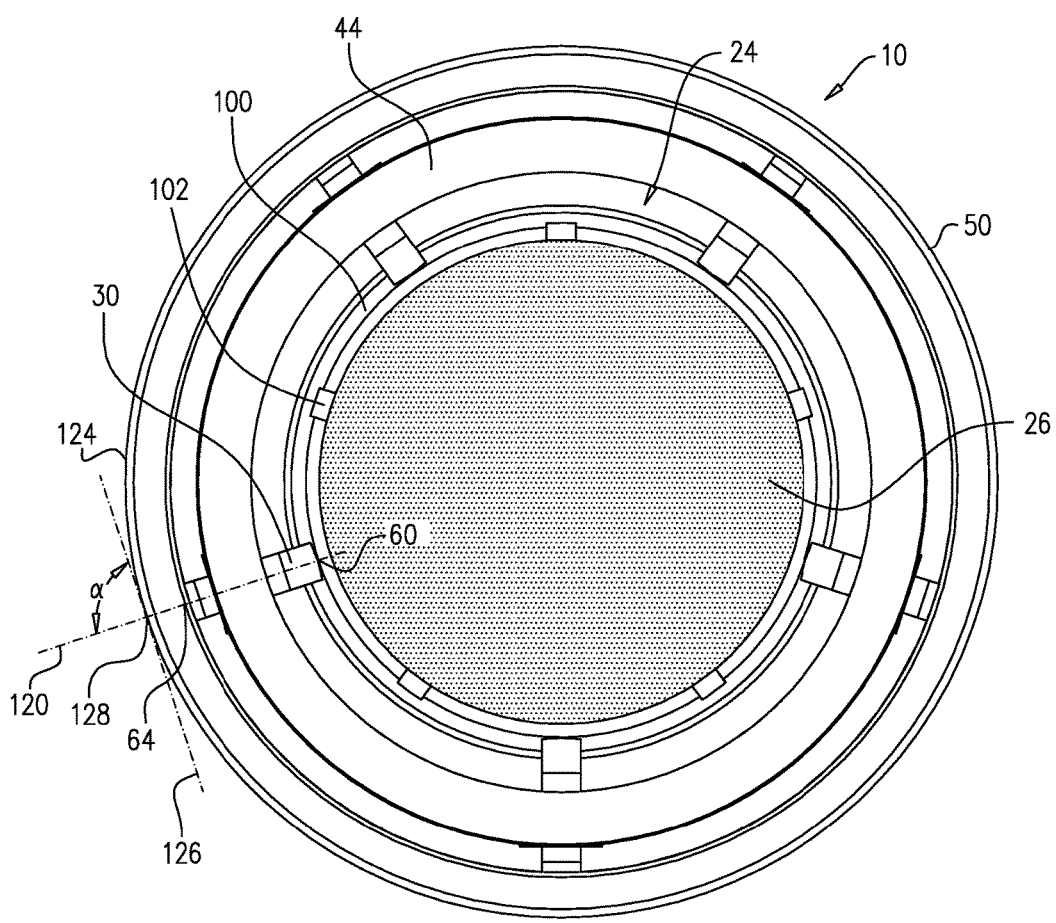
FIG. 8 is a schematic anterior view of the lens implant of FIGS. 1A-C and 2A-C, in accordance with an application of the present invention.

Reference is made to FIG. 8, which is a schematic anterior view of lens implant 10, in accordance with an application of the present invention. For some applications, for each respective lever 30 of levers 30, (a) a straight line 120 defined by first longitudinal site 60 of the respective lever 30 and third longitudinal site 64 of the respective lever 30, when projected onto a plane defined by a radially-outer perimeter 124 of accommodating intraocular lens implant 10, and (b) a straight line 126 that is in the plane and that is tangential to radially-outer perimeter 124 at a circumferential site 128 of radially-outer perimeter 124 circumferentially corresponding to third longitudinal site 64 of respective lever 30, form an angle α (alpha) of between 75 and 105 degrees, such as 85 to 95 degrees, e.g., 90 degrees (as shown).

Figure 9:
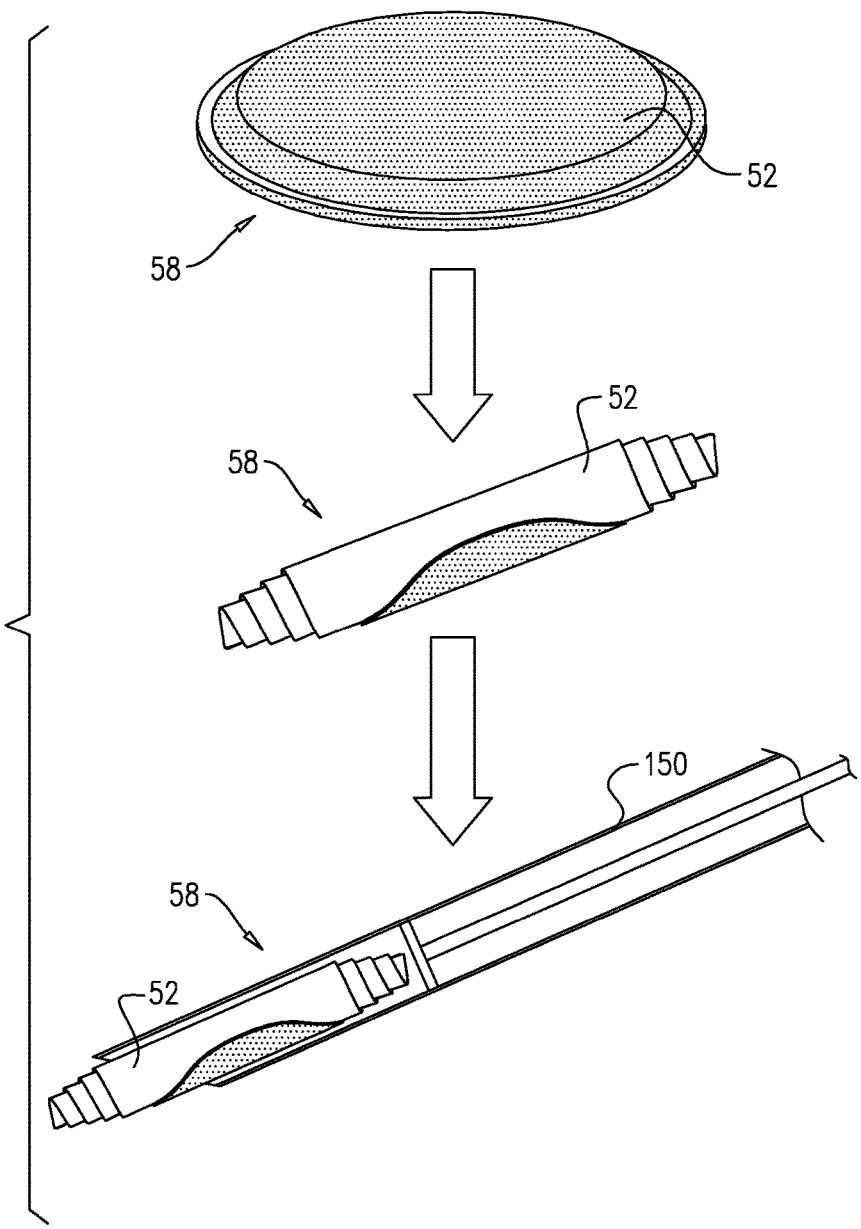
FIG. 9 is a schematic illustration of the removable disposal of a second posterior component of the lens implant of FIGS. 1A-C and 2A-C in a first introducer tube, in accordance with an application of the present invention.

Reference is made to FIG. 9, which is a schematic illustration of the removable disposal of second posterior component 58 of lens implant 10 in a first introducer tube 150, in accordance with an application of the present invention. As shown in FIG. 9, second posterior component 58 (which comprises posterior lens 52) is removably disposed in first introducer tube 150 while rolled.

Figure 10:
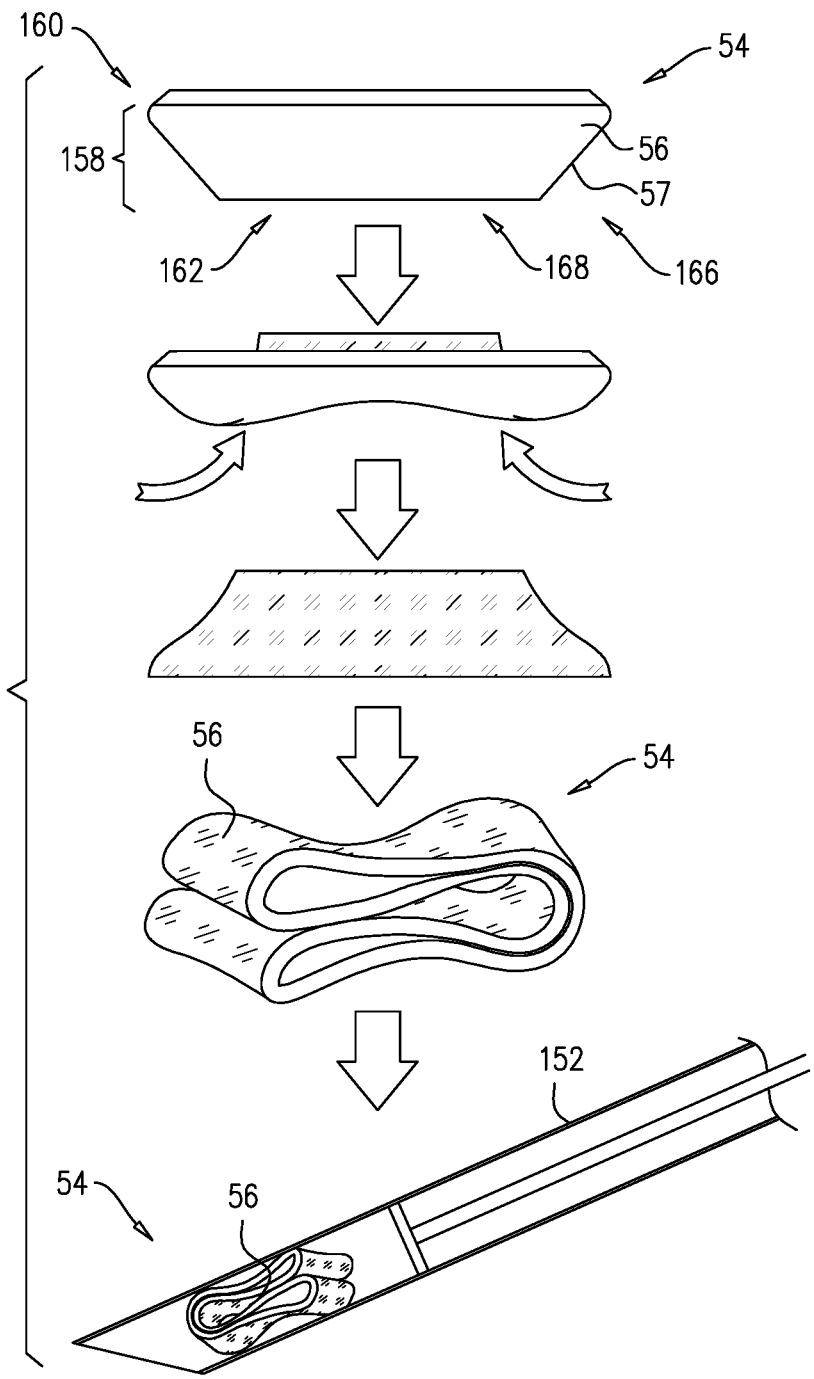
FIG. 10 is a schematic illustration of the removable disposal of a posterior lens rim of a first posterior component of the lens implant of FIGS. 1A-C and 2A-C in a second introducer tube, in accordance with an application of the present invention.

Reference is made to FIG. 10, which is a schematic illustration of the removable disposal of posterior lens rim 56 of first posterior component 54 of lens implant 10 in a second introducer tube 152, in accordance with an application of the present invention. For some applications, as shown in FIG. 10, posterior lens rim 56 of first posterior component 54 is removably disposed in second introducer tube 152 while folded or rolled. For some applications, posterior lens rim 56, when in an unconstrained state, includes a frustoconical portion 158 and defines larger and smaller openings 160 and 162. Posterior lens 52 is insertable into and coupleable with smaller opening 162. For some applications, posterior lens rim 56 is removably disposed in second introducer tube 152 while posterior lens rim 56 is inverted from its unconstrained state and folded or rolled. For some applications, posterior lens rim 56, when in the unconstrained state, is shaped so as to define a posterior surface 57 which is convex (configuration not shown), rather than a posterior surface 57 which is strictly frustoconical as shown.

For some applications, posterior lens rim 56 is removably disposed in second introducer tube 152 while folded in half (configuration not shown). For some applications, posterior lens rim 56, when in an unconstrained state, is shaped as a partial bowl 166 surrounding an opening 168 into which posterior lens 52 is insertable; posterior lens rim 56 is placed (and removably disposed) in second introducer tube 152 while bowl 166 is inverted from its unconstrained state and folded in half.

For some applications, as shown in FIG. 10, posterior lens rim 56 is placed (and removably disposed) in second introducer tube 152 while folded in quarters. For some applications, posterior lens rim 56, when in an unconstrained state, is shaped as partial bowl 166 surrounding opening 168 into which posterior lens 52 is insertable; posterior lens rim 56 is removably disposed in second introducer tube 152 while bowl 166 is inverted from its unconstrained state and folded in quarters.

Reference is made to FIG. 11, which is a schematic illustration of the removable disposal of anterior assembly 18 of lens implant 10 in a third introducer tube 154, in accordance with an application of the present invention.

Reference is made to FIGS. 12A-M, which are schematic illustrations of a method of implanting intraocular lens implant 10, in accordance with an application of the present invention. This three-step insertion procedure generally allows the use of a smaller incision than is necessary for a one-step insertion procedure of a single-piece implant. Typically, upon assembly, all of the rings and lenses of lens implant 10 are concentric.

As shown in FIGS. 12A-C, a natural lens 180 is removed from a human eye 182, such as using conventional techniques known in the art. For example, as shown in FIG. 12B, an anterior capsulectomy may be made using continuous curvilinear capsulorhexis (CCC).

Figure 12D:
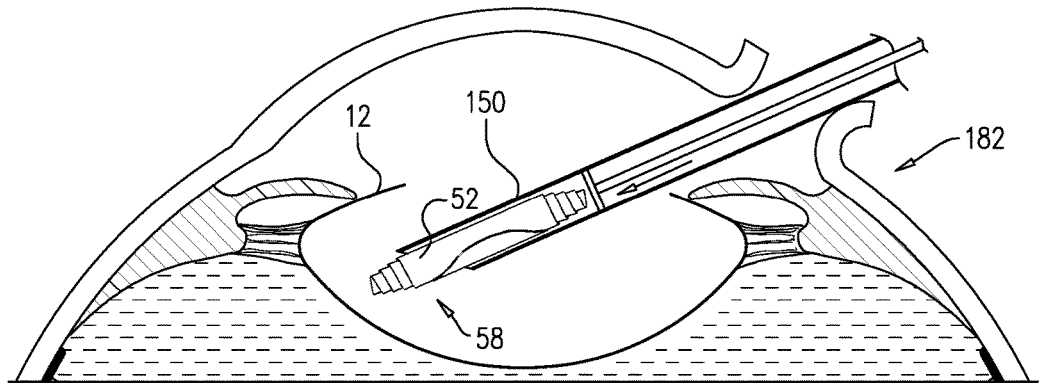
Figure 12E:
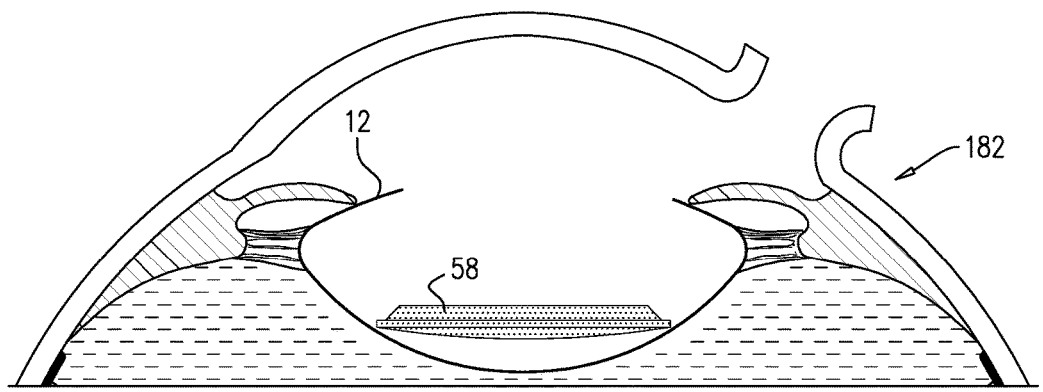

As shown in FIGS. 12D-E, first introducer tube 150 is inserted into capsular bag 12 of eye 182, and second posterior component 58 (which comprises posterior lens 52) is released from the introducer tube in capsular bag 12 and positioned posteriorly in capsular bag 12.

As shown in FIGS. 12F-K, second introducer tube 152 is inserted into capsular bag 12 of eye 182, and posterior lens rim 56 of first posterior component 54 is released from the introducer tube in capsular bag 12, is allowed to unfold or unroll in capsular bag 12, and is assembled in situ with second posterior component 58, such that posterior lens rim 56 radially surrounds at least axial portion 59 of posterior lens 52, as shown in FIG. 12K. For some applications, first and second posterior components 54 and 58 have matching beveled edges; second posterior component 58 is moved with respect to first posterior component 54 until the components align and become coupled together.

For some applications (configuration not shown), posterior lens rim 56 is introduced into capsular bag 12 folded or rolled, without being removably disposed in an introducer tube.

The scope of the present invention includes performing the steps of the method described with reference to FIGS. 12F-K before performing the steps of the method described with reference to FIGS. 12D-E.

Figure 12F:
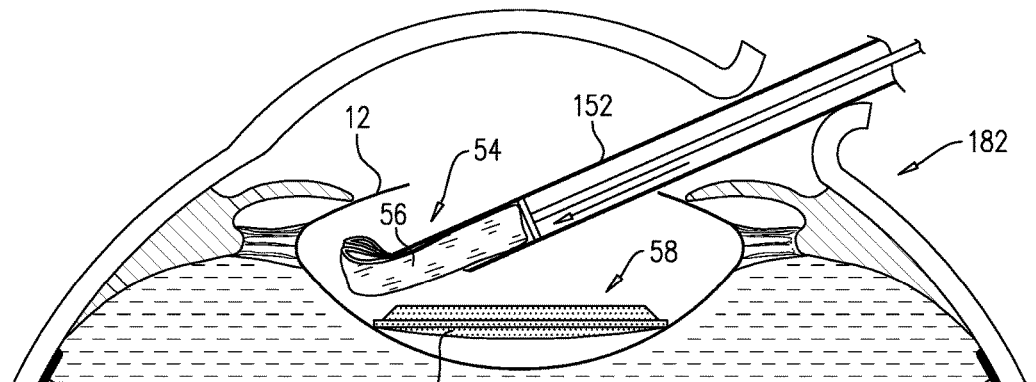
Figure 12G:
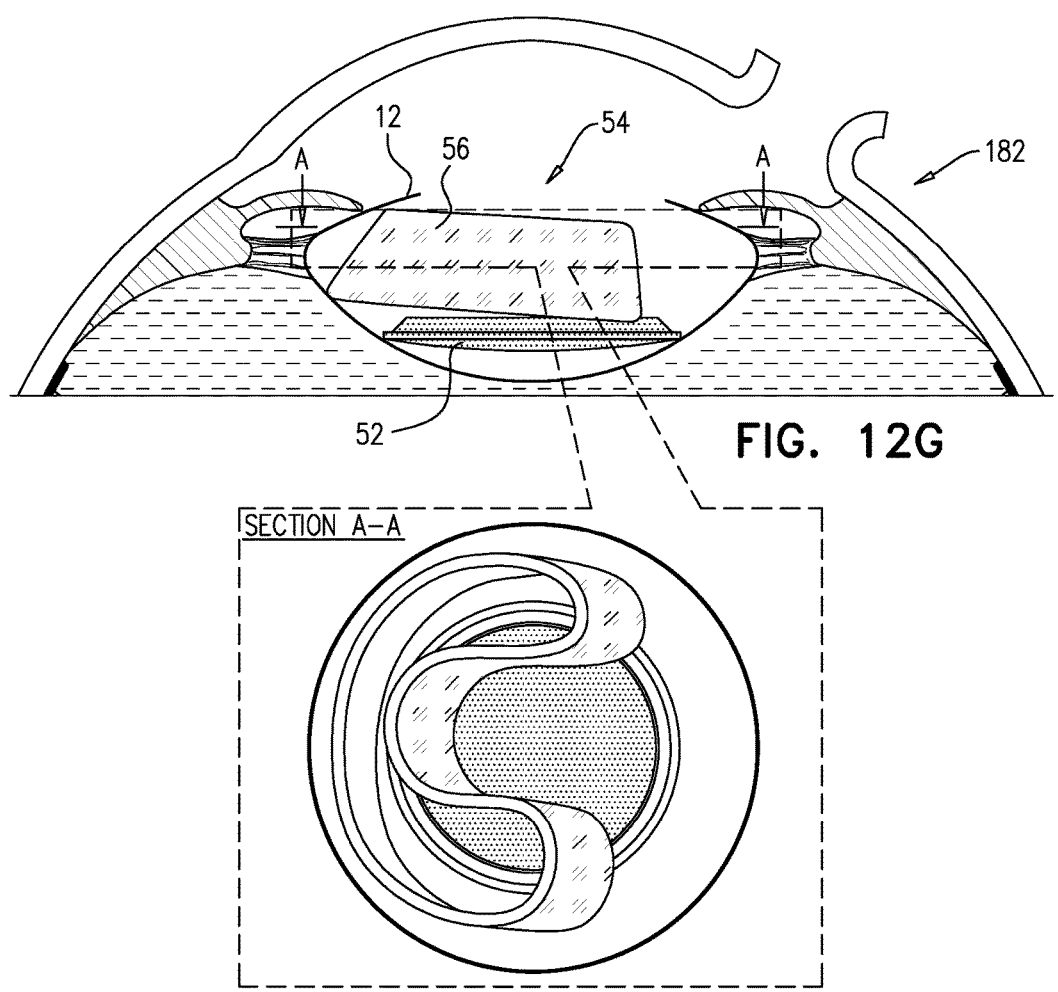

The inventors hypothesize that for many applications, the insertion of posterior lens rim 56 shown in FIG. 12F and the transition of the shape and position of posterior lens rim 56 from as shown in FIG. 12F to as shown in FIG. 12H are facilitated by posterior lens rim 56 having been inverted as shown in the sequence of steps in FIG. 10 prior to placement in second introducer tube 152. In particular, this inversion in some cases may reduce the likelihood of posterior lens rim 56 exiting the opening in capsular bag 12 after having been partially placed into capsular bag 12. The inversion shown in FIGS. 12H-J may occur by itself, typically fairly quickly (because of the shape memory of the material), or may require some gentle prodding by the surgeon.

Figure 12L:
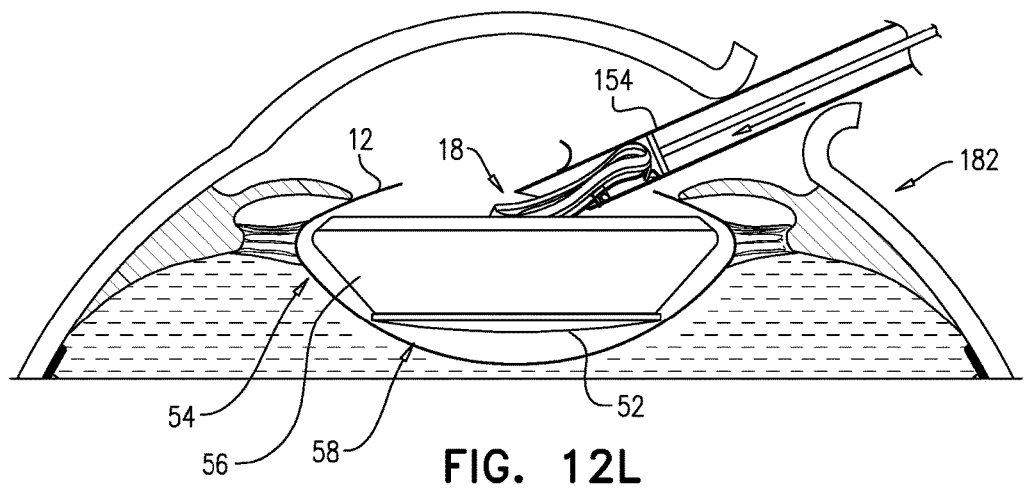
Figure 12M:
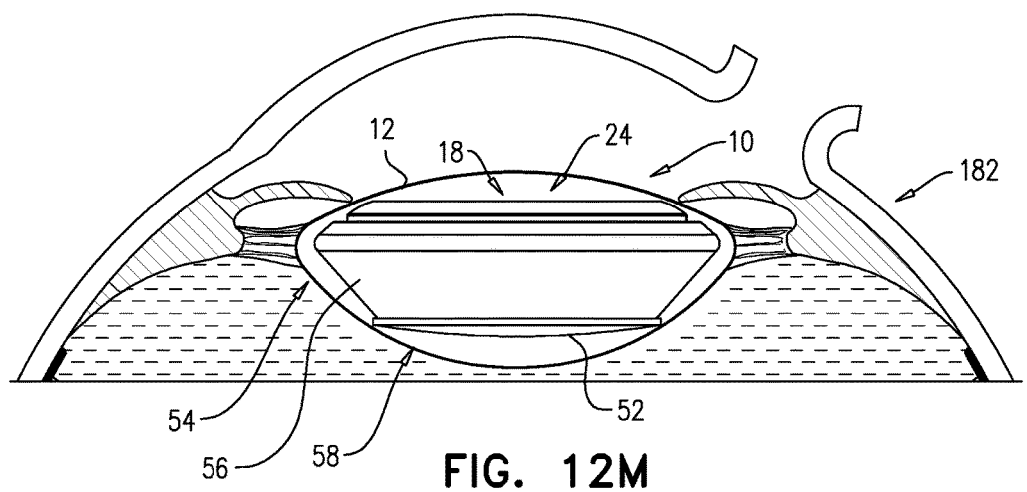

As shown in FIGS. 12L-M, after first and second posterior components 54 and 58 have been released into capsular bag 12, third introducer tube 154 is inserted into capsular bag 12 of eye 182, and anterior assembly 18, including anterior lens 26 of anterior floating lens unit 24, is released from the introducer tube in capsular bag 12. Anterior floating lens unit 24 is coupled to second posterior component 58, as shown in FIG. 12M, thereby completing the implantation procedure.

For some applications, a single introducer tube is used to introduce all of the components of lens implant 10. Alternatively, for some applications, exactly two introducer tubes are used to introduce all of the components of lens implant 10, i.e., two of the components described above are introduced in a first introducer tube, and the third component is introduced in a second introducer tube.

For some applications, posterior lens 52 is inserted into capsular bag 12 after posterior lens rim 56 is released from introducer tube 150 in capsular bag 12. Alternatively, posterior lens 52 is inserted into capsular bag 12 before posterior lens rim 56 is released from introducer tube 150 in capsular bag 12.

Reference is now made to FIGS. 1A-10I. For some applications, as shown in the figures, lens implant 10 does not comprise any haptics.

Although the two-part design of lens implant 10 has been described as being use for an accommodating IOL, the two-part design may also be used in non-accommodating and single lenses as well.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus comprising an accommodating intraocular lens implant, which comprises:
    an anterior floating lens unit, which comprises (a) an anterior lens, (b) an anterior lens ring, which has a diameter greater than that of the anterior lens, and (c) rim-connector elements, which are distributed around the anterior lens ring at respective connector sites, and connect the anterior lens ring to the anterior lens such that the anterior lens ring does not directly contact the anterior lens;
    a posterior lens unit, which comprises a posterior lens;
    an anterior rim complex; and
    between three and eight levers, which are (a) (i) in jointed connection with the anterior lens ring of the anterior floating lens unit at respective first longitudinal sites along the levers, (ii) in pivotable connection with the anterior rim complex at respective second longitudinal sites along the levers, and (iii) in pivotable contact with the posterior lens unit at respective third longitudinal sites along the levers, and (b) arranged to move the anterior floating lens unit toward and away from the anterior rim complex, in an anterior-posterior direction,
    wherein the accommodating intraocular lens implant is configured such that the anterior lens ring deforms during a transition of the accommodating intraocular lens implant between a fully-accommodated state and a fully-unaccommodated state,
    wherein the lens implant is configured such that the levers move the anterior floating lens unit by a first anterior-posterior distance with respect to the posterior lens unit when the anterior rim complex moves a second anterior-posterior distance with respect to the posterior lens unit, the first distance greater than the second distance,
    wherein the levers are connected to respective lever-ring sites around the anterior lens ring, at the respective first longitudinal sites along the levers, and
    wherein the connector sites and the lever-ring sites are circumferentially offset from one another and alternate with one another around the anterior lens ring.

2. The apparatus according to claim 1,
    wherein the anterior lens ring has a circularly-curved longitudinal axis around the anterior lens ring, and
    wherein the accommodating intraocular lens implant is configured such that the anterior lens ring twists around the circularly-curved longitudinal axis during the transition of the accommodating intraocular lens implant between the fully-accommodated state and the fully-unaccommodated state.

3. The apparatus according to claim 1, wherein the levers and the posterior lens unit are distinct from each other, and are shaped so as to be assemblable together in situ in a capsular bag of a human eye.

4. The apparatus according to claim 1, wherein, for each respective lever of the levers, the second longitudinal site is longitudinally between the first and the third longitudinal sites along the respective lever, such that the third longitudinal site serves as a fulcrum for the respective lever.

5. The apparatus according to claim 4, wherein the respective third longitudinal sites are disposed at greater distances from a central optical axis of the lens implant than the respective second longitudinal sites are from the central optical axis, the distances measured perpendicular to the central optical axis.

6. The apparatus according to claim 5, wherein the respective second longitudinal sites are disposed at greater distances from the central optical axis than the respective first longitudinal sites are from the central optical axis, the distances measured perpendicular to the central optical axis.

7. The apparatus according to claim 1, wherein each of the lever-ring sites is circumferentially centered between two circumferentially-adjacent ones of the connector sites.

* * * * *